(12) United States Patent
Estes et al.

(10) Patent No.: US 9,409,173 B2
(45) Date of Patent: Aug. 9, 2016

(54) METHOD AND DEVICE FOR GENERATING A TUNABLE ARRAY OF FLUID GRADIENTS

(71) Applicant: The Arizona Board of Regents on behalf of The University of Arizona, Tucson, AZ (US)

(72) Inventors: Matthew D Estes, Phoenix, AZ (US); Cedric M Hurth, Tempe, AZ (US); Frederic Zenhausern, Fountain Hills, AZ (US)

(73) Assignee: The Arizona Board of Regents on Behalf of The University of Arizona, Tucson, AZ (US)

( * ) Notice: Subject to any disclaimer, the term of this patent is extended or adjusted under 35 U.S.C. 154(b) by 0 days.

(21) Appl. No.: 14/092,239

(22) Filed: Nov. 27, 2013

(65) Prior Publication Data

US 2014/0162262 A1 Jun. 12, 2014

Related U.S. Application Data

(60) Provisional application No. 61/797,139, filed on Nov. 30, 2012.

(51) Int. Cl.
*B01L 3/00* (2006.01)
*G01N 33/53* (2006.01)
*B01F 13/00* (2006.01)
(Continued)

(52) U.S. Cl.
CPC ....... *B01L 3/502776* (2013.01); *B01F 13/0059* (2013.01); *B01F 15/0404* (2013.01); *G01N 33/5304* (2013.01); *B01L 7/52* (2013.01); *B01L 2200/0636* (2013.01); *B01L 2200/0694* (2013.01); *B01L 2300/0816* (2013.01); *B01L 2400/0472* (2013.01);
(Continued)

(58) Field of Classification Search
CPC ............ B01F 13/0059; B01F 15/0404; B01L 2200/0636; B01L 2200/0694; B01L 2300/0816; B01L 2400/0472; B01L 3/502776; G01N 33/5304
See application file for complete search history.

(56) References Cited

U.S. PATENT DOCUMENTS 7,112,444 B2 9/2006 Beebe et al.
7,314,070 B2 1/2008 Jeon et al.
(Continued)

OTHER PUBLICATIONS

Abhyankar et al. (2006) "Characterization of a Membrane-Based Gradient Generator for Use in Cell-Signaling Studies," *Lab Chip.* 6:389-393.
(Continued)

*Primary Examiner* — Jennifer Wecker
(74) *Attorney, Agent, or Firm* — Lathrop & Gage LLP

(57) ABSTRACT

Provided herein are devices and methods for generating microfluidic gradients, including an array of unique microfluidic gradients within an array of microchannels. Fluids within conduits are mixed in an intersection region to generate a mixed flow stream in a source reservoir channel that provides a gradient that varies with axial distance from the intersection region. Microchannels having an inlet connected to the source reservoir channel are configured to provide a microfluidic gradient in the microchannel. An outlet end of the microchannel is connected to a sink reservoir channel. By varying the ratio of fluid flow rates from the fluid conduits, the microchannel gradients are tuned. In this manner, a large number of unique gradients or array of microfluidic gradients is provided, wherein the gradient can be any number of physical or chemical parameters, including concentrations and physical fluid properties.

18 Claims, 8 Drawing Sheets

(51) Int. Cl.
  *B01F 15/04* (2006.01)
  *C12Q 1/42* (2006.01)
  *B01L 7/00* (2006.01)
(52) U.S. Cl.
  CPC ... *B01L 2400/0487* (2013.01); *Y10T 29/49826* (2015.01); *Y10T 436/25* (2015.01)

(56) References Cited

U.S. PATENT DOCUMENTS

| | | | |
|---|---|---|---|
| 7,470,403 B2 | 12/2008 | Beebe et al. | |
| 7,837,379 B2 | 11/2010 | Fiering et al. | |
| 7,947,491 B2 | 5/2011 | Jeon et al. | |
| 8,021,480 B2 | 9/2011 | Hansen et al. | |
| 8,333,934 B2* | 12/2012 | Cao et al. | 422/502 |
| 8,377,685 B2 | 2/2013 | Meyvantsson et al. | |
| 2002/0113095 A1* | 8/2002 | Jeon et al. | 222/424.5 |
| 2010/0290309 A1* | 11/2010 | Glazier et al. | 366/154.1 |
| 2011/0244567 A1* | 10/2011 | Jeon et al. | 435/373 |
| 2012/0100538 A1* | 4/2012 | Mikolajczyk et al. | 435/6.11 |

OTHER PUBLICATIONS

Ahmed et al. (2010) "Bacterial chemotaxis in linear and nonlinear steady microfluidic gradients," *Nano Lett.* 10:3379-3385.
Alsayed et al. (2007) "Mechanisms of Regulation of CXCR4/SDF-1 (CXCL12)-Dependent Migration and Homing in Multiple Myeloma," *Blood.* 109:2708-2717.
Amadi et al. (2010) "A low resistance microfluidic system for the creation of stable concentration gradients in a defined 3D microenvironment," *Biomed. Microdevices.* 12:1027-1041.
Amarie et al. (2007) "Compact Microfluidic Structures for Generating Spatial and Temporal Gradients," *Anal. Chem.* 79:9471-9477.
Atencia et al. (2009) "The microfluidic palette: A diffusive gradient generator with spatio-temporal control," *Lab Chip.* 9:2707-2714.
Atencia et al. (2012) "A robust diffusion-based gradient generator for dynamic cell assays," *Lab Chip.* 12:309-316.
Baker et al. (2012) "Deconstructing the third dimension—how 3D culture microenvironments alter cellular cues," *J. Cell Sci.* 125:3015-3024.
Bennet et al. (2009) "Microfluidic devices for measuring gene network dynamics in single cells," *Nat. Rev.: Gen.* 10:628-638.
Brett et al. (2012) "A Microfluidic Device that Forms and Redirects Pheremone Gradients to Study Chemotropism in Yeast," *Lab Chip*, 12:3127-3134.
Burg (2003) "Suspended Microchannel Resonators for Biomolecular Detection," *Appl. Phys. Lett.* 83:2698-2700.
Chen et al. (2011) "Generation of oxygen gradients in microfluidic devices for cell culture using spatially confined chemical reactions," *Lab Chip.* 11:3626-3633.
Chen et al. (2012) "A microfluidic concentration generator for dose-response assays on ion channel pharmacology," *Lab Chip*, 2012,12,794-801.
Cheng et al. (2007) "A Hydrogel-Based Microfluidic Device for the Studies of Directed Cell Migration," *Lab Chip*, 2007,7,763-769.
Chung et al. (2005) "Human Neural Stem Cell Growth and Differentiation in a Gradient-Generating Microfluidic Device," *Lab Chip*, 2005, 5, 401-406.
Comelles et al. (2012) "Versatile Gradients of Covalently Bound Proteins on Microstructured Substrates," *Langmuir.* 28:13688-13697.
Dertinger et al. (2001) "Generation of Gradients Having Complex Shapes Using Microfluidic Networks," *Anal. Chem.* 73:1240-1246.
Dertinger et al. (2002) "Gradients of substrate-bound laminin orient axonal specification of neurons," *Proc. Natl. Acid. Sci. U. S. A.*, 2002, 99, 12542-12547.
Estes et al. (2012) "Optimization of multiplexed PCR on an integrated microfluidic forensic platform for rapid DNA analysis," *Analyst.* 137:5510-5519.
Estes et al. (Apr. 2013) "A tunable array of unique steady-state microfluidic gradients," *Phys. Chem. Chem. Phys.* 15:12805-12814.

Estes (Sep. 25, 2013) "A Linear Array of Unique Microfluidic Gradients for Enzymatic Bioassay," In; Lab-on-a-Chip World Congress. San Diego, CA, USA.
Fosser et al. (2003) "Fabrication of patterned multicomponent protein gradients and gradient arrays using microfluidic depletion," *Anal. Chem.* 75:5775-5782.
Fujii et al. (2006) "Microbioassay system for an anti-cancer agent test using animal cells on a microfluidic gradient mixer," *Anal. Sci.* 22:87-90.
Georgescu et al. (2007) "Model-Controlled Hydrodynamic Focusing to Generate Multiple Overlapping Gradients of Surface-Immobilized Proteins in Microfluidic Devices," *Lab Chip*, 2007, 8, 238-244.
Glawdel et al. (2009) "Microfluidic system with integrated electroosmotic pumps, concentration gradient generator and fish cell line (RTgill-W1)—towards water toxicity testing," *Lab Chip*, 2009, 9, 3243-3250.
Hatch et al. (2001) "A rapid diffusion immunoassay in a T-sensor," *Nat. Biotechnol.* 19:461-465.
Holden et al. (2003) "Generating fixed concentration arrays in a microfluidic device," *Sens. Actuators. B* 92:199-207.
Hopwood et al. (2010) "Integrated Microfluidic System for Rapid Forensic DNA Analysis: Sample Collection to DNA Profile," *Anal. Chem.* 82:6991-6999.
Hsu et al. (2006) "Spatiotemporally-Complex Concentration Profiles Using a Tunable Chaotic Micromixer," *Appl. Phys. Lett.*, 2006, 89, 144102.
Hurth et al. (2010) "An automated instrument for human STR identification: Design, characterization, and experimental validation," *Electrophoresis.* 31:3510-3517.
Irimia et al. (2006) "Universal Microfluidic Gradient Generator," *Anal. Chem.* 78:3472-3477.
Jeon et al. (2000) "Generation of Solution and Surface Gradients Using Microfluidic Systems," *Langmuir.* 16:8311-8316.
Jeon et al. (2002) "Neutrophil chemotaxis in linear and complex gradients of interleukin-8 formed in a microfabricated device," *Nat. Biotechnol.* 20:826-830.
Jeon et al. (2009) "Design and simulation of passive mixing in microfluidic systems with geometric variations," *Chem. Eng. J.* 152:575-582.
Kamholz et al. (1999) "Quantitative Analysis of Molecular Interaction in a Microfluidic Channel: The T-Sensor," *Anal. Chem.* 71:5340-5347.
Kamholz et al. (2001) "Optical Measurement of Transverse Molecular Diffusion in a Microchannel," *Biophys. J.* 80:1967-1972.
Kamholz et al. (2001) "Theoretical analysis of molecular diffusion in pressure-driven laminar flow in microfluidic channels," *Biophys. J.* 80:155-160.
Keenan et al. (2008) "Biomolecular gradients in cell culture systems," *Lab Chip.* 8:34-57.
Kim et al. (2009) "Selective and tunable gradient device for cell culture and chemotaxis study," *Lab Chip.* 9:1797-1800.
Kim et al. (2010) "Biological applications of microfluidic gradient devices," *Integr. Biol.* 2:584-603.
Lagunas et al. (2010) "Universal chemical gradient platforms using poly(methyl methacrylate) based on the biotin-streptavidin interaction for biological applications," *Langmuir.* 26:14154-14161.
Lee et al. (2009) "Generalized serial dilution module for monotonic and arbitrary microfluidic gradient generators," *Lab Chip.* 2009, 9, 709-711.
Li et al. (2011) "Microfluidic devices for studying chemotaxis and electrotaxis," *Trends Cell Biol.* 21:489-497.
Li et al. (2012) "Microfluidic device for studying cell migration in single or co-existing chemical gradients and electric fields," *Biomicrofluidics.* 6:024121.
Lin et al. (2004) "Generation of dynamic temporal and spatial concentration gradients using microfluidic devices," *Lab Chip.* 4:164-167.
Lin et al. (2006) "T cell chemotaxis in a simple microfluidic device," *Lab Chip.* 6:1462-1469.
Liu et al. (2008) "Microfluidic switching system for analyzing chemotaxis responses of wortmannin-inhibited HL-60 cells," *Biomed. Microdevices*, 2008, 10, 499-507.

(56) References Cited

OTHER PUBLICATIONS

Mao et al. (2003) "A sensitive, versatile microfluidic assay for bacterial chemotaxis," *Proc. Natl. Acad. Sci. U. S. A.*, 2003, 100, 5449-5454.

Moore et al. (2008) "Robust Spatial Sensing of Mating Pheromone Gradients by Yeast Cells," *PLoS One*. 3:e3865.

Mosadegh et al. (2007) "Generation of Stable Complex Gradients Across Two-Dimensional Surfaces and Three-Dimensional Gels" *Langmuir*. 23:10910-10912.

Nguyen et al. (2005) "Micromixers—a review," *J. Micromech. Microeng.* 15:R1-R16.

Pihl (2005) "Microfluidic Gradient-Generating Device for Pharmacological Profiling," *Anal. Chem.* 77:3897-3903.

Rosa et al. (2012) "High-throughput study of alpha-synuclein expression in yeast using microfluidics for control of local cellular microenvironment," *Biomicrofluidics*. 6:014109.

Saadi et al. (2007) "Generation of stable concentration gradients in 2D and 3D environments using a microfluidic ladder chamber," *Biomed. Microdevices*. 9:627-635.

Sahai et al. (2011) "Microfluidic chip with temporal and spatial concentration generation capabilities for biological applications," *Microelec. Eng.* 88:1689-1692.

Shamloo et al. (2008) "Endothelial cell polarization and chemotaxis in a microfluidic device," *Lab Chip*. 8:1292-1299.

Song et al. (1997) "cAMP-induced switching in turning direction of nerve growth cones," *Nature*. 388:275-279.

Srisa-Art et al. (2008) "Monitoring of real-time streptavidin-biotin binding kinetics using droplet microfluidics," *Anal. Chem.*, 2008, 80, 7063-7067.

Steinberg et al. (2003) "Global quantitative phosphoprotein analysis using Multiplexed Proteomics technology," *Proteomics*, 2003, 3, 1128-1144.

VanDersarl et al. (2011) "Rapid spatial and temporal controlled signal delivery over large cell culture areas," *Lab Chip*. 11:3057-3063.

Walker et al. (2005) "Effects of flow and diffusion on chemotaxis studies in a microfabricated gradient generator," *Lab Chip*. 5:611-618.

Wu et al. (2006) "Generation of Complex, Static Solution Gradients in Microfluidic Channels," *J. Am. Chem. Soc.* 128:4194-4195.

Zaari et al. (2004) "Photopolymerization in Microfluidic Gradient Generators: Microscale Control of Substrate Compliance to Manipulate Cell Response," *Adv. Mater.* 16:2133-2137.

\* cited by examiner

METHOD AND DEVICE FOR GENERATING A TUNABLE ARRAY OF FLUID GRADIENTS

CROSS-REFERENCE TO RELATED APPLICATIONS

This application claims the benefit of U.S. Provisional Application No. 61/797,139, filed Nov. 30, 2012, which is hereby incorporated by reference in its entirety to the extent not inconsistent herewith.

BACKGROUND OF THE INVENTION

The devices and methods provided herein relate to microfluidic design and control so as to precisely, accurately and reliably tune dynamic components of a fluid. In this manner, an array of microfluidic gradients can be produced simultaneously without any need for fluid valves or other complicated flow control elements.

The ability to precisely and reliably deliver materials has a number of important applications, ranging from surface processing, chemical or biological reactions, assays, materials and biological research, clinical diagnostics, and other related applications known by those skilled in the art. Furthermore, of interest is the ability to provide gradients of a parameter, such as a concentration gradient, including for biological applications where chemical gradients rather than simply the presence or absence of a chemical is important. Much research and development has been centered on platforms and methods for generating gradients, including U.S. Pat. Nos. 7,470,403; 7,314,070; 8,377,685; 7,837,379; 7,112,444; 7,947,491; and 8,021,480, for example. Although that work offers unique profile intensities, unique profile shapes, or tunability, there is a need for a platform that allows for all three of these crucial criteria to be probed and/or manipulated. Presented herein are methods and devices that provide the ability to simultaneously and in a parallel manner, generate uniquely shaped gradients with controlled magnitudes, wherein on-the-run tuning permits the selection of desired gradient shapes and magnitudes. Such methods and devices represent a fundamental improvement in the art and may be employed in any number of wide-ranging applications.

SUMMARY OF THE INVENTION

Devices and methods are provided that rely on the combination of a special fluidic configuration and flow regimes that result in the ability to obtain spatio-temporal control or tuning of any of a wide range of parameters that are affected or provided by fluid flow and diffusive processes. By specially mixing two or more fluid streams and providing the two or more flow streams in a source reservoir channel, a well-defined gradient is achieved in a source reservoir channel, with a gradient of a parameter of interest varying with axial distance from the mixing region. A microchannel or microchannel array is fluidically connected to the source reservoir channel and configured with a high fluidic resistance to fluid flow from the source reservoir channel. This is achieved, for example, by making the cross-sectional area of each microchannel to fluid flow small. Under these conditions, diffusive forces dominate so that a gradient is also provided to each of the microchannels. Accordingly, the methods and devices provided herein provide control of two different gradients: (1) a gradient in a source reservoir channel provided by the flow of mixed fluid comprising two distinct flow streams; and (2) a gradient in the microchannel due predominantly, as desired, to diffusion. Due to the gradient in the source reservoir channel, the gradient in each of the microchannels (for embodiments where there is an array of microchannels) may be unique, with the gradient dependent in part on the magnitude of the parameter presented to the inlet of each microchannel. The methods and devices provided herein are extremely versatile and are suitable in any number of applications and for any number or kinds of gradients, ranging from gradients of physical parameters of fluid such as temperature, viscosity, polymerization, to physical-chemical parameters such as concentrations, product generation from chemical reactions, to bioparameters such as cellular responses, characterizations, sequencing and for any number of binding events. This wide-spread versatility is a reflection that the methods and devices provide a number of technical benefits that are not achieved, or are not easily achieved, in the art, including the ability to rapidly, efficiently and precisely deliver a well-defined gradient to a plurality of microchannels. Provided herein is control that is referred herein as "spatio-temporal" control because the gradient may be precisely controlled or varied with respect to spatial location and/or may be controlled or varied with respect to time.

Provided herein are methods and devices such as a microfluidic gradient generator that allows for steady state programming of the intensities of a parameter of interest across multiple orders of magnitude while producing exponential, linear, and logarithmic gradient profiles of the parameter of interest both within and across microchannels. The magnitude of the gradient intensities may be controlled in part through regulating the ratio of two on-chip flow inlets without the need for valves or other active mixers. The device geometry together with the flow rate and localized chemical interactions are configured to provide programmable or user-controllable gradient intensity of many microchannels in parallel or simultaneously. The ability to simultaneously carry out several distinct experiments is beneficial for the multiplexed study of bioprocesses across varying intensities and time scales for a given biomolecule of interest, thereby decreasing both time and money without sacrifice in experimental fidelity or reliability. The methods and devices allow for generating both unique gradient profile shapes and intensities in parallel, along with mechanical design configuration to facilitate on-the-fly customization of steady state intensities across a wide array of continuous values. This is accomplished without the need for on-chip active controls such as valves. This provides a platform having a broad range of applications, spanning from engineering to life sciences. The steady state programming of a wide variety of unique gradient profiles in parallel while providing continuous temporal tuning of the gradients disclosed herein satisfies a need in the art for a platform that can reliably control and utilize all three of: (1) unique gradient intensities/magnitudes; (2) unique gradient shapes, and (3) gradient tunability.

In an aspect, the device is described as a microfluidic gradient generator. The generator is capable of tuning dynamic components of fluid, such as fluid composition, concentrations, chemical reaction products, temperature, electrical conductivity, viscosity or any other parameter that may be affected, influenced or controlled by a flow of fluid in combination with diffusion. The device may comprise a first fluid conduit, a second fluid conduit and an intersection region that fluidically connects the first fluid conduit and the second fluid conduit. The intersection region may comprise an intersection opening between the first fluid conduit and the second fluid conduit and a flow-divider that extends in a downstream direction from the intersection opening. A source reservoir channel fluidically connects to the intersection region and extends downstream from the intersection opening and a sink reservoir channel fluidically connects to the intersection region and extends downstream from the intersection opening. A microchannel or a microchannel array comprising a plurality of microchannels, each microchannel having an inlet end connected to the source reservoir channel and an outlet end connected to the sink reservoir channel, wherein adjacent microchannels are separated from each other by a separation distance and the microchannel array traverses an axial distance along the source reservoir channel. The first fluid conduit and the second fluid conduit are configured to provide to the intersection region a ratio of a first fluid flow rate to a second fluid flow rate to establish a mixed flow that is substantially laminar, the mixed flow comprising the first fluid and the second fluid in the source reservoir channel. The mixed flow in the source reservoir channel also establishes a source reservoir channel gradient along with a microfluidic gradient or an array of microfluidic gradients that vary with the ratio of the first fluid flow rate to the second fluid flow rate. Any of the devices or methods provided herein comprise a single microchannel, providing a single microfluidic gradient. Alternatively, any of the devices or methods provided herein comprise an array of microchannels, thereby providing an array of microfluidic gradients with each microchannel providing a corresponding microfluidic gradient and the combination of the all the microfluidic gradients forming the array of microfluidic gradients.

Any of the methods, systems, or devices described herein having an array of microchannels may instead have a single microchannel, wherein instead of the array of microchannels a single microchannel is employed. This aspect is useful for applications where only a single microchannel is required and remains advantageous in that the gradient within the microchannel is well-controlled, monitored and all focus may be directed to the single microchannel. Accordingly, in any of the disclosure herein the term "array of microchannels" may be replaced with the term "microchannel" and correspondingly the term "array of microfluidic gradients" replaced with the term "microfluidic gradient".

In an aspect, the microchannel is configured to provide an axial-varying gradient, such as by providing small cross-section microchannels to ensure diffusive forces dominate so that the gradient will be governed by the diffusion equation. Alternatively, the microchannel cross-section can be increased to decrease the dominance of diffusion related to a pressure-driven bulk fluid flow, thereby changing the microfluidic gradient. In an aspect, bulk flow through the microchannel may be increased sufficiently so as to provide a gradient that at least in part along the microchannel approaches zero or is zero. In an embodiment, the flow in the system is continuous or at a constant flow rate. Alternatively, the flow in the system may be pulsatile or pulsed flow, defined by a user-selected frequency and amplitude.

Any of the devices provided herein may orient the plurality of microchannels in an axial direction that is substantially perpendicular to an axial direction of the source reservoir channel.

In an embodiment, the source reservoir channel and the sink reservoir channel extend along an axial direction, wherein the source reservoir axial direction and the sink reservoir axial direction are substantially parallel to each other and separated by a separation distance through which the array of microchannels traverse.

In an aspect, any of the devices further comprise an outlet conduit, wherein the source reservoir channel and the sink reservoir channel join downstream of the microchannel array to form the outlet conduit. Such a configuration may be beneficial as providing a pressure balance between the source and sink reservoir channels so that microchannels positioned downstream and closer the outlet have little pressure difference between the inlet and outlet, resulting in substantially purely diffusive driven gradients. This results in a substantially linear microfluidic gradient in the microchannel. In contrast, for microchannels that are further upstream from the outlet conduit, there may be a correspondingly higher pressure difference, with a larger component of pressure-driven or convective fluid flow that impacts the microfluidic gradient in the upstream-positioned microchannel. This results in a microfluidic gradient having a more curved gradient profile, such as a more exponential gradient profile. This is one mechanism wherein the device provides unique microfluidic gradient shapes within the array of microfluidic gradients.

The microfluidic gradient generator may be provided with any number of microchannels, as desired. In one example, the plurality of microchannels number from a range that is greater than or equal to 2 and less than or equal to 100. The microchannels may be equally spaced relative to each other. Alternatively, the microchannels may be not equally spaced relative to other microchannels. Alternatively, one portion of the microchannels may have equal spacing, and at least another portion that is unequally spaced. Such unequally spaced configurations are desirable where higher sensitivity is desired in a particular gradient regime without sacrificing the ability to provide microfluidic gradients that differ by orders of magnitude.

Any of the devices provided herein may be described in terms of one- or more physical characteristics. The methods and systems provided herein, however, are not constrained to any particular dimensions, so long as the fluidic characteristics allow for the generation of tunable gradients along the source reservoir channel and, as desired, corresponding array of microfluidic gradients over the array of microchannels. Certain exemplary ranges are provided herein, for example, the microchannels of the microchannel array may independently have a cross-sectional area that is less than or equal to 0.1 $mm^2$ and a length that is greater than or equal to 0.1 mm and less than or equal to 1 cm. The microchannels of the microchannel array may independently have a volume that is greater than or equal to 1 nL and less than or equal to 1 mL, such as between about 20 nL and 100 µL. The source and sink reservoir channels may each independently have a cross-sectional area that is greater than or equal to 1 $mm^2$ and less than or equal to 1 $cm^2$ and a length that is greater than or equal to 1 mm and less than or equal to 10 cm. The first and second fluid conduits may each independently have a cross-sectional area that is greater than or equal to 1 $mm^2$ and less than or equal to 1 $cm^2$, and an intersection angle relative to each other that is less than 180°. Preferably, the cross-sectional areas, fluid flow-rates, fluid properties, and microfluidic gradient generator geometry are configured to provide substantially laminar flow at and downstream of the intersection region. The devices and methods, however, tolerate a certain amount of turbulence and in aspects localized turbulence may be desired so as to further influence source reservoir channel gradient and corresponding array of microfluidic gradients.

The microarray of channels may be formed in a base plate and the source and sink reservoir in a top plate, with the bottom plate and top plate connected to form the microarray of channels positioned in a different plane from the source and the sink reservoir channels. The base plate and the top plate may be connected with an adhesive so as to fluidically connect the desired components with each other. This is a particularly advantageous configuration as it facilitates culture of biological cells in desired locations, such as in the array of microchannels only, the source and/or reservoir changes, the first and/or second fluid conduits, or any combination thereof. For examples, cells may be grown in the fluid conduits that secrete a bioagent or bioactive agent that can be characterized or tested in the array of microchannels. Similarly, a chemical or other agent may be tested against a biological cell by proving the chemical or other agent to cells that are supported by the microarray that were cultured on the bottom plate.

Any of the devices provided herein may further comprise an intersection opening having an opening length that is greater than a diameter of a microchannel in the microchannel array and less than twice a width of the source or the sink reservoir channel. The flow-divider may comprise an upstream sharp-edged divider that defines the downstream side of the intersection opening. The flow-divider may further comprise a downstream reservoir separation section that separates the source and sink reservoir channels and an expanding central section that connects the upstream sharp-edged divider to the downstream reservoir separation section.

In an aspect, the microchannel array traverses the downstream reservoir separation section to fluidically connect the source and sink reservoir channels. In this aspect, each microchannel of the array may have an equivalent length. In an aspect, the diameter or cross-sectional area of each microchannel is the same. In an aspect, they may have different sizes, thereby providing additional control of the microfluidic gradient within an individual microchannel.

Each microchannel inlet end may be positioned on a bottom surface of the source reservoir channel and each microchannel outlet end may be positioned on a bottom surface of the sink reservoir channel. The microchannels may be formed in a different plane that is positioned beneath the reservoir channels, thereby providing a perturbance on the surface to create additional passive mixing to assist in differentiating the distinct gradient profile for each microchannel in the array. Such a configuration is further beneficial in allowing a more robust fabrication process, and decreasing tolerances required during alignment of the top and bottom plates. Optionally, the inlet on the bottom surface may be described as occupying a certain percentage of the width of the source reservoir channel and/or the sink reservoir channel, such as substantially the entire width of the bottom surface, or between about 25% and 100% of the width of the channel, or between about 50% and 95% of the width. Optionally, the width of the microchannels that protrude into the bottom surface of the channels is substantially uniform across at least the central 95% of the length of the microchannel.

In another embodiment, any of the microfluidic gradient generators have a microchannel inlet end positioned on a lumen-facing surface of the source reservoir channel.

The first fluid inlet conduit and sink reservoir channel may form a mirror image of the second fluid inlet and source reservoir channel. Accordingly, the sink and source reservoir channels are interchangeable by providing an inverse of the ratio of the first fluid flow rate to the second fluid flow rate.

One of the benefits of the instant devices and related methods, are that any of the microfluidic gradients may have any number of shapes, such as a shape that is not-linear or a shape that is linear. Similarly, flow conditions and geometries may be selected to provide a source reservoir gradient that is linear, not linear, or a combination of linear and not linear. In this manner, any of the systems and methods may focus on a precise portion of the gradient magnitude to provide high-sensitivity, while simultaneously spanning many orders of magnitude, particularly when paired with selective placement of microchannels within the microchannel array.

In an aspect, the microfluidic gradient is selected from the group consisting of: concentration of a material suspended in the first fluid; concentration of a material suspended in the second fluid; ratio of the first fluid amount to the second fluid amount; temperature; electrical conductivity; binding event; amplification of template biomolecules; concentration of a product produced by a substrate-enzyme reaction in the mixed fluid of the source reservoir channel; concentration of a bioproduct produced from combination of a first biomolecule in the source reservoir channel and a second biomolecule in the microchannels; and a biological event characterized by an interaction between a material suspended or formed in the mixed fluid flow and a biological cell in the microarray.

As discussed, the microfluidic gradient is configured for high sensitivity at a user-selected magnitude and that optionally spans up to five orders of magnitude. The specific details of sensitivity depend on the parameter that forms the gradient. For example, if the parameter is concentration, "high sensitivity" may refer to the ability to reliably establish a concentration difference in the nanomolar range, being able to reliably establish a concentration in one microchannel at a position that differs from another microchannel by 1 µM, 1 nM or 1 pM or sub-femtomolar. In the context of a molecular event, such as binding, high sensitivity may refer to the ability to provide and/or distinguish events between adjacent microchannels that number as few as 100, 10 and up to a single binding event.

Any of the microfluidic gradient generators may further comprise a flow-rate controller to vary the ratio of the first fluid flow rate to the second fluid flow rate, wherein the flow-rate controller provides a microfluidic gradient having a shape and a magnitude that is temporally adjustable. Any means for controlling fluid flow rates may be used, such as pumps, hydrostatic flow devices, or the like. One fluid controller may be used to control one of the fluid flow rates or, for further flexibility, two fluid controllers are provided for independent flow rate control of both inlets. As desired, additional fluid flow inlets may be incorporated, as desired so long as a desired mixed flow in the source reservoir channel is maintained.

The devices may include a first fluid in the first fluid conduit and a second fluid in the second fluid conduit, wherein a chemical or a biochemical is transported in the first fluid, the second fluid, or both, and the microfluidic gradient is concentration of the chemical or biochemical in each of the microchannels. Chemical or biochemical is used broadly to refer to any material where a concentration gradient is desired, such as for the chemical or biochemical itself, or a product of a reaction, or a biological event such as a binding event.

In an aspect, the device further comprises biological cells supported by a surface of the microchannel array for testing the effect of different concentrations of the chemical or biochemical on the biological cells. This can be useful in any number of assays, screens, or toxicity tests. Accordingly, the devices and processes are compatible with any number or types of chemicals or biochemical, such as: a cancer treatment candidate; a reagent compound for performing a biological assay reaction; a drug for toxicity screening; a growth factor for cellular differentiation; a ligand that specifically binds a surface receptor; an immunoactive agent for chemotaxis or immunological study; a chemical for a polymerization reaction; a chemical for a catalytic reaction; a chemical for a synthesis; a radionuclide reaction; an energy conversion reaction, and a reagent for amplification of polynucleotides by an enzymatic reaction such as polymerase chain reaction, rolling circle replication (RCA) isothermal reaction and/or by direct signal amplification, such as by quantitative nuclease protection assay (qNPA), chemical ligation dependent probe amplification (CLPA) or other reaction involving analytes selected from the groups consisting of proteins, peptides, polysaccharides, lipids or hybrid biomaterials.

Depending on the parameter that is desired to be controlled by the gradient, the array of microfluidic gradients may correspond to a physical parameter selected from the group consisting of temperature, pH, oxygen level, electrical conductivity, a rheological property, electromagnetic property, light emission, light absorption, and adsorption. Many of these parameters are controlled by controlling the composition of the mixed fluid that is introduced to the microchannel. For example, by providing one fluid stream of high temperature (pH, oxygen level, electrical conductivity, etc.) and the other fluid stream that is lower, a gradient is established in the source reservoir channel, which then diffuses into the microchannels, thereby providing the array of microfluidic gradients.

Any of the devices and systems provided herein may be used for treating surfaces of the array of microchannels. For example, different surface concentration coatings may be applied, such as by adsorption of a chemical or biochemical introduced at different concentrations to the microchannels of the array.

In an aspect, the source reservoir channel gradient and the microfluidic gradient are each steady-state gradients. This is achieved, for example, by maintaining the fluid flow rate ratio constant for a sufficiently long time to establish a steady-state gradient. Alternatively, the gradients may vary temporally such as by varying a fluid flow rate, and therefore ratio of flow rates.

In an embodiment, each of the first fluid and the second fluid comprise a liquid. The invention, however, encompasses fluids that are gases and/or mixtures of gases and liquids.

Any of the microfluidic gradient generators described herein may comprise a base plate and a top plate that are connected to each other to form the fluid conduits, reservoir channels, microchannel array, and intersection region. For example, the microchannel array may be formed on one of the base or top plates, and the other fluidic components in the other plate. In this manner, cultured biological cells may be supported by the microchannel array formed in the plate so that after connecting the plates, the cells are well-confined to the microchannel array. Similarly, cells or different cell types may be provided to other portions of the device, such as the first or second fluid conduit, or the reservoir channels.

In another embodiment, the invention is a method of using any of the devices described herein to provide the ability to tune dynamic components of fluid.

For example, provided is a method of generating an array of microfluidic gradients by flowing a first fluid in a first fluid conduit at a first fluid flow rate ($Q_1$), flowing a second fluid in a second fluid conduit at a second flow rate ($Q_2$) and introducing the first fluid and the second fluid to an intersection region. In this manner, an inlet fluid flow ratio, $Q_i$, is defined and calculated as: $Q_i = Q_1/Q_2$. The inlet fluid flow ratio is selected to generate a mixed flow comprising the first fluid and the second fluid, wherein the mixed flow is substantially laminar in a source reservoir channel fluidly connected to the intersection region to provide a source reservoir channel gradient, wherein the source reservoir channel gradient varies with a longitudinal distance from the intersection region by diffusion between the first fluid and the second fluid in the source reservoir channel. The mixed flow is introduced from the source reservoir channel to an array of microchannels, wherein each microchannel has a microchannel inlet fluidically connected to the source reservoir channel and a microchannel outlet fluidically connected to a sink reservoir channel, and each microchannel is separated from an adjacent microchannel by a microchannel separation distance. The sink reservoir channel is fluidically connected to the intersection region and the sink reservoir channel and source reservoir channel are separated from each other by the microchannel array. The source reservoir channel gradient provides an array of microfluidic gradients in the array of microchannels that is tunable by varying the inlet fluid flow ratio, thereby generating a tunable array of microfluidic gradients. In this manner, the method may be described as having a unique microfluidic gradient in each microchannel.

In an embodiment, the inlet fluid flow ratio is greater than or equal to 2 and less than or equal to 1000, and fluid flow in each of the intersection region, source reservoir channel and sink reservoir channel is substantially laminar and each microfluidic gradient in a microchannel is different from another microfluidic gradient in another microchannel.

The method may further comprise the step of filling the sink reservoir channel with the first fluid and providing an excess of the first fluid to the source reservoir channel to provide the mixed stream flow in the source reservoir channel with the first fluid functioning as a diffusive barrier between the second fluid and the microchannel inlet ends. This configuration is useful for providing gradients of a material (e.g., chemical or biochemical) that is suspended in the second fluid to the microchannels, thereby generating an array of microfluidic gradients.

Any of the methods may further comprise the step of adjusting the inlet fluid flow ratio to tune the array of microfluidic gradients.

In an embodiment, the method further comprises the step of inverting the inlet fluid flow ratio thereby switching the position of the source and sink reservoir channels.

In an aspect, any of the methods are directed to the first fluid flow rate that is greater than the second fluid flow rate, and the second fluid flow rate that is maintained constant and the first fluid flow rate is adjusted, wherein a lower first fluid flow rate provides relatively higher concentration of second fluid in the source reservoir channel available at the microchannel inlets, and a higher first fluid flow rate provides a relatively lower concentration of the second fluid in the source reservoir channel available at the microchannel inlets. In this manner, magnitude of the gradient may be controlled.

The method may further comprise increasing or decreasing the first fluid flow rate to the intersection region, thereby increasing or decreasing a boundary thickness between the second fluid in the source reservoir channel and the microchannel inlets. The boundary thickness adjustment in the source reservoir channel is another means of influencing magnitude of the gradient.

In an aspect, the second fluid flow rate is selected from a range that is greater than or equal to 0.1 µL/min and less than or equal to 100 µL/min.

In an aspect, the reservoir channel Reynolds number is less than or equal to 100 and the microchannel Reynolds number that is less than or equal to 1. In an aspect, the Peclet number in the array of microchannels is less than 10 and a Peclet number in the source reservoir channel is least 1000-times greater than the Peclet number in the array of microchannels.

In an aspect, the number of microchannels in the microchannel array is selected from a number that is greater than or equal to two and less than or equal to 100.

In aspects where the number of microchannels in the microchannel array is greater than two, the microchannels may be uniformly spaced or not uniformly spaced with respect to each other. In an aspect, the microchannel separation distance may be selected from a range that is greater than or equal to 10 μm and less than or equal to 1 cm.

The source and sink reservoir channels may be aligned in a direction substantially parallel to each other and the array of microchannels aligned in a direction substantially perpendicular to the direction of the source and sink reservoir channels. In an aspect, the source and sink reservoir channels join at position downstream of the array of microchannels The intersection region may be configured to balance pressure between the source and sink reservoir channels, thereby maintaining a high fluidic resistance in the array of microchannels to provide predominately diffusive communication between the mixed flow stream and the array of microchannels.

The intersection region may comprises an acute incident angle between the first fluid conduit and the second fluid conduit, an intersection opening having an opening length that is less than about a width of the first fluid conduit or the second fluid conduit to provide mixing between the first and second fluids, and a flow-divider positioned downstream of the intersection opening that divides the source reservoir channel from the sink reservoir channel.

Any of the methods provided herein may further comprise the step of tuning the source reservoir channel gradient by adjusting fluid flow inlet ratio, thereby changing the array of microfluidic gradients.

The methods are useful for obtaining an array of microfluidic gradients, such as microfluidic gradients that correspond to one or more of: a concentration of a material transported from the source reservoir channel to the array of microchannels; a temperature in the array of microchannels, a fluid composition in the array of microchannels, a fluid electrical conductivity in the array of microchannels, a binding event in the array of microchannels; a collision or combination event between molecules; or an amplification of analytes in the array of microchannels.

Any of the methods provided herein further comprise the step of providing a chemical or biochemical in the second fluid and providing excess first fluid to the source reservoir channel, wherein the source reservoir channel gradient corresponds to a concentration of the chemical or biochemical in the source reservoir channel provided to the array of microchannels, thereby providing an array of microfluidic gradients corresponding to a gradient of chemical or biochemical concentration in the plurality of microchannels. In this aspect, each of the microchannels itself has a gradient along the microchannel such as caused by diffusion from the inlet (higher concentration) toward the outlet (lower concentration).

The method may further comprise the step of obtaining an array of microfluidic gradients, wherein each microfluidic gradient in a microchannel has a gradient shape that is linear, exponential, logarithmic, or a combination thereof. In an aspect, the shape of the gradient in the microchannel may depend on the position of the microchannel. For example, an upstream microchannel may have a microfluidic gradient shape that is exponential and a downstream microchannel may have a microfluidic gradient shape that is linear.

The method may further comprise the step of adjusting a microchannel array property to obtain a desired microfluidic gradient or an array of microfluidic gradients, wherein the microchannel array property is selected from the group consisting of: microchannel diameter, microchannel length, microchannel separation distance, microchannel surface treatment, and a combination thereof. For example, increasing the microchannel diameter decreases fluidic resistance, thereby allowing a larger flow of mixed fluid by convection, compared to diffusion, thereby changing the gradient magnitude and shape.

The method may further comprise the step of inverting the inlet fluid flow ratio to generate an opposite overlapping gradient direction across the microchannel array for a second agent of interest conveyed by the first fluid. This provides additional versatility to the system, with gradients decreasing toward the outlet or toward the inlet and can be useful in any number of applications.

In an aspect, the method relates to use of biological cells, such as by providing biological cells to the array of microchannels and supplying a chemical or biochemical to the second fluid. The inlet fluid flow rate ratio is selected to provide the source reservoir channel gradient that corresponds to concentration of the bioactive agent at the microfluidic array inlet ends. The effect on the biological cells is examined at different concentrations of the chemical or biochemical. This method provides high throughput screening via the array of microfluidic gradients in a single experiment.

In an aspect, the biological cell is a tumor cell and the chemical or biochemical is a candidate for the treatment of cancer.

The chemical or biochemical may selected from the group consisting of a therapeutic candidate, a ligand, a receptor for a ligand, a fluorescent dye, a bioactive agent, an enzyme in a chemical reaction, a substrate in a chemical reaction, a biomarker, a polynucleotide, a nucleic acid, a protein, a polypeptide, a lipid, a small molecule, a sugar, a metabolite, a bacteria, a virus, and a fungus.

In an aspect, the first fluid comprises a first agent and the second fluid comprises a second agent, wherein the first agent and second agent are a noncovalent binding pair or an enzyme-substrate pair.

The method may further comprise varying the inlet flow rate ratio to vary microfluidic gradient intensity, microfluidic gradient shape, or both. The microfluidic gradient and source reservoir channel gradient may be steady-state gradients. The method may further comprise the step of controlling the microfluidic gradient by controlling a binding event in the array of microchannels to independently adjust a diffusive barrier to the mixed fluid in the source reservoir channel.

Any of the methods may be used in an application selected from the group consisting of: biomolecule characterization; chemical reaction characterization; pharmacokinetic drug study; drug response study; sequencing analysis; toxicity study; genomics; proteomics; metabolomics; epigenomics; chemotaxis, temperature gradient response, cancer metastasis; stem cell differentiation; infection and/or immune response; electrical stimulation; neural development; and biological response of a cellular system.

Also provided are devices for carrying out any of the methods disclosed herein.

In another embodiment, the invention is a method of making any of the microfluidic gradient generators described herein. The method may comprise forming a fluidic network comprising a source reservoir channel, a sink reservoir channel, a first fluid conduit, a second fluid conduit, and an intersection region in a top plate, wherein the first and second fluid conduits fluidically connect with each other at the intersection region, and the source and sink reservoir channels fluidically connect to the intersection region and extend downstream of the intersection region. An array of microchannels is formed in a bottom plate. The top plate and the bottom plate are connected, wherein the array of microchannels extend between and fluidically connect the source reservoir channel and the sink reservoir channel, thereby forming the microfluidic gradient generator.

The plates may be formed of glass, plastic, polymers, semiconductor materials, hybrid nanomaterials, ceramics or equivalent thereof. The fluid networks and components may be mass-produced, such as by injection molding process, CNC (computer numerical control), hot embossing, nanoimprinting, contact printing, or other preferably highly automated processes.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

DETAILED DESCRIPTION OF THE INVENTION

Figure 1:
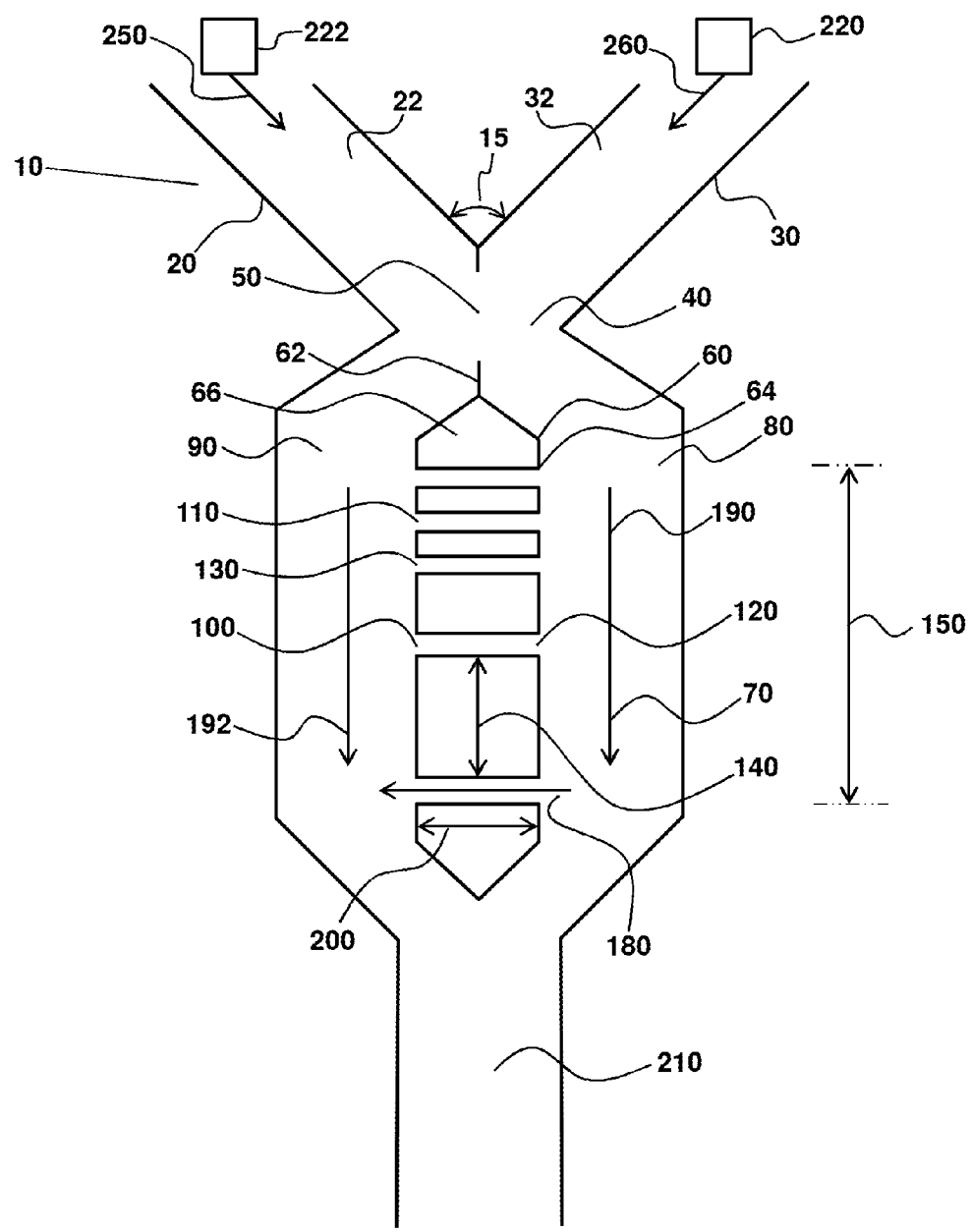
FIG. 1 is a schematic illustration of a microfluidic gradient generator for tuning dynamic components of fluid.

In general, the terms and phrases used herein have their art-recognized meaning, which can be found by reference to standard texts, journal references and contexts known to those skilled in the art. The following definitions are provided to clarify their specific use in the context of the invention. "Gradient" is used broadly herein to refer to a varying physical or chemical property.

"Microfluidic gradient generator" refers to any of the devices described herein that is capable of tuning a dynamic component of a fluid and presenting that dynamic component in the form of a microfluidic gradient.

"Dynamic components of fluid" refers to a parameter associated with a fluid that may be reliably controlled and changed so as to generate a microfluidic gradient thereof. As the methods and devices herein are suitable for establishing gradients for a wide range of parameters that may be generally characterized as physical, chemical, or biological in nature, "dynamic components" is used broadly herein. Components include physical-type parameters such as temperature, frequency, viscosity, concentrations, compositions, electrical conductivity, electromagnetic property, density. Component may also include chemically-based parameters, such as resulting from a chemical reaction or interaction such as adsorption to a surface. Component may also further include a characterization of an event, such as a biological event, a binding event, an assay output.

"Microfluidic gradient" accordingly, refers to a magnitude profile of any of the dynamic components or other parameter of interest, specifically in the context of a microchannel. Due to the configuration of the devices provided herein, the microfluidic gradient generally refers to the gradient profile as a function of axial position along the microchannel. "Microchannel" refers to a fluid conduit or channel having at least one dimension that is less than 1 mm in size, and more preferably a cross-sectional area relative to the direction of diffusion or fluid flow that is less than 1 $mm^2$ and more preferably less than 0.1 mm². Alternatively, a microchannel may generally refer to a channel designed so that the gradient magnitude and profile is predominantly governed or has a substantial contribution by diffusion.

"Reservoir channel gradient" refers to the mix-fluid flow in the source reservoir channel, wherein one fluid shields another fluid from being able to penetrate to a microchannel inlet. In particular, laminar flow streams do not bulk mix as occurs during turbulent flow, so that any mixing is predominantly via diffusion between the two streams. This is a mechanism wherein a reservoir channel gradient is established, tending to have lowest magnitude upstream and highest magnitude downstream. A desired magnitude may be established by varying the ratio of the fluid flow rates at the intersection region.

"Microfluidic gradient" is used broadly herein to refer to the gradient in a microchannel. "Array of microfluidic gradients" refers to the combination of all microfluidic gradients in each microchannel within the array of microchannels, and further emphasizes that due to the gradient in the source reservoir channel providing differing magnitudes depending on the position of each microchannel inlet along the source reservoir channel, the microfluidic gradients in the microchannels may differ from each other. Accordingly, certain systems and devices provided herein are characterized as being capable of providing a tunable array of unique microfluidic gradients. A unique result of the processes and devices provided herein is the ability to control a number of different "gradients", such as: (1) gradient in the source reservoir channel; (2) gradient along the microchannel inlets; (3) gradient within a microchannel (arising from diffusion from the microchannel inlet toward the microchannel outlet, or vice versa); and (4) gradient between microchannels. Adjusting various parameters will affect the types of gradients differently. For example, microchannel diameter and position may locally affect gradient within the microchannel. Varying flow-rates will affect the gradient in the source reservoir channel and along the microchannel inlets. Introduction of special fluids and materials suspended in the fluids can affect microfluidic gradient, array of microfluidic gradients and source reservoir channel gradient. In this manner, precise and independent control can be achieved to obtain desired gradient characteristics.

"Source reservoir channel" refers to a fluid conduit having a parameter of interest that is provided to the microchannel(s). In contrast, a "sink reservoir channel" may be a conduit opposed to the source reservoir channel having a minimum or no parameter present. In this manner, diffusion occurs in the direction from the source to the sink. Although source and sink are exemplified herein, one skilled in the art will recognize the terms may be interchanged simply by introducing different fluid mixes having different parameters or components of interest. For instance, a first dynamic component may be in the source channel that diffuses from the source to the sink, but with respect to a second component, the second component may diffuse from the sink to the source. In other words, with respect to the second component, the sink is actually the source and the source is actually the sink.

"Laminar" refers to fluid flow in which viscous forces predominate and may be characterized by a Reynolds number that is small. Depending on geometry, flow conditions and level of flow perturbances, flow may be considered laminar for Reynolds numbers up to about 2000, less than about 1000, less than 100 or less than 1. Laminar flow is characterized by well-defined fluid flow streamlines that do not mix via a convective mechanism. Instead, the predominate mixing mechanism is by diffusion between streamlines. "Substantially laminar" refers to portions of the fluid flow that may have localize turbulence but without unduly disturbing the diffusive effect that provides the ability to control and obtain desired microfluidic gradients in a particular microchannel or a gradient with respect to the plurality of microchannels.

Unless defined otherwise, "substantially" may refer to a value that is within 10%, within 5%, or within 1% of a desired value, and includes values that correspond to a desired value.

"Tuning" or "tunable" refers to the ability to select a desired microfluidic gradient or array of microfluidic gradients. The tuning may be by simply adjusting relative flow rates without the need for any other fluid control elements, such as valves.

"Fluidically connected" refers to a fluid or fluid property being able to transit, either under a bulk flow or by diffusion, between components without impacting the desired function of the components.

"Chemical or biochemical" is used broadly herein, such as any material that is suspended in and transported by a fluid and that can, according to the invention provided herein, result in a concentration gradient. Both terms are used to clarify that the application may be either non-biological or biological in nature.

"Steady-state gradient" refers to a gradient, including a source reservoir channel gradient, a microfluidic gradient, or array of microfluidic gradients, that does not substantially deviate over time. The devices and methods provided herein are particularly suited for generating steady-state gradients, useful for many applications, by simply maintaining a the flow rate ratio ($Q_1/Q_2$).

The invention may be further understood by the following non-limiting examples. All references cited herein are hereby incorporated by reference to the extent not inconsistent with the disclosure herewith. Although the description herein contains many specificities, these should not be construed as limiting the scope of the invention but as merely providing illustrations of some of the presently preferred embodiments of the invention. The scope of the invention, therefore, should be determined by the appended claims and their equivalents, rather than by the examples given.

FIG. 1 is a schematic illustration of a microfluidic gradient generator 10. The generator 10 is configured for tuning dynamic components of fluid, such as concentrations of materials suspended in the fluid or any other parameter of interest ranging from a physical parameter, a chemical parameter, a biological event or response, or a reaction/binding event. First fluid conduit 20 and second fluid conduit 30 fluidically connect at an intersection region 40, such as an intersection region comprising an intersection opening 50. The connection may be further described by an incident angle 15. Intersection region 50 defines a point at which a first fluid 22 and a second fluid 32 contained in respective fluid conduits, intimately meet to generate a mixed flow. For turbulent flow, the fluids may become uniformly mixed. For laminar flow, in contrast, each of the flowstreams provided by first fluid flow and second fluid flow do not mix, except by diffusion between the flowstreams. Accordingly, for laminar flows and first fluid flow rate 250 that is significantly greater than second fluid flow rate 260, a boundary layer is effectively formed in mixed fluid flow that flows down source reservoir channel 80 formed via flow-divider 60 that extends in a downstream direction 70 from the intersection region 40 and intersection opening 50. As used herein, upstream refers to a direction that is toward fluid inlets 20 and 30, whereas downstream is in the direction of the arrow 70 which indicates direction of fluid flow.

To facilitate desired fluid flow mixing in the intersection region 40 and subsequent flow in the source reservoir 80, a sharp-edged divider 62, downstream reservoir separation section 64 and an expanding central section 66 that connects the downstream reservoir separation section 64 and the sharp-edged divider 62 may be employed.

Figure 2:
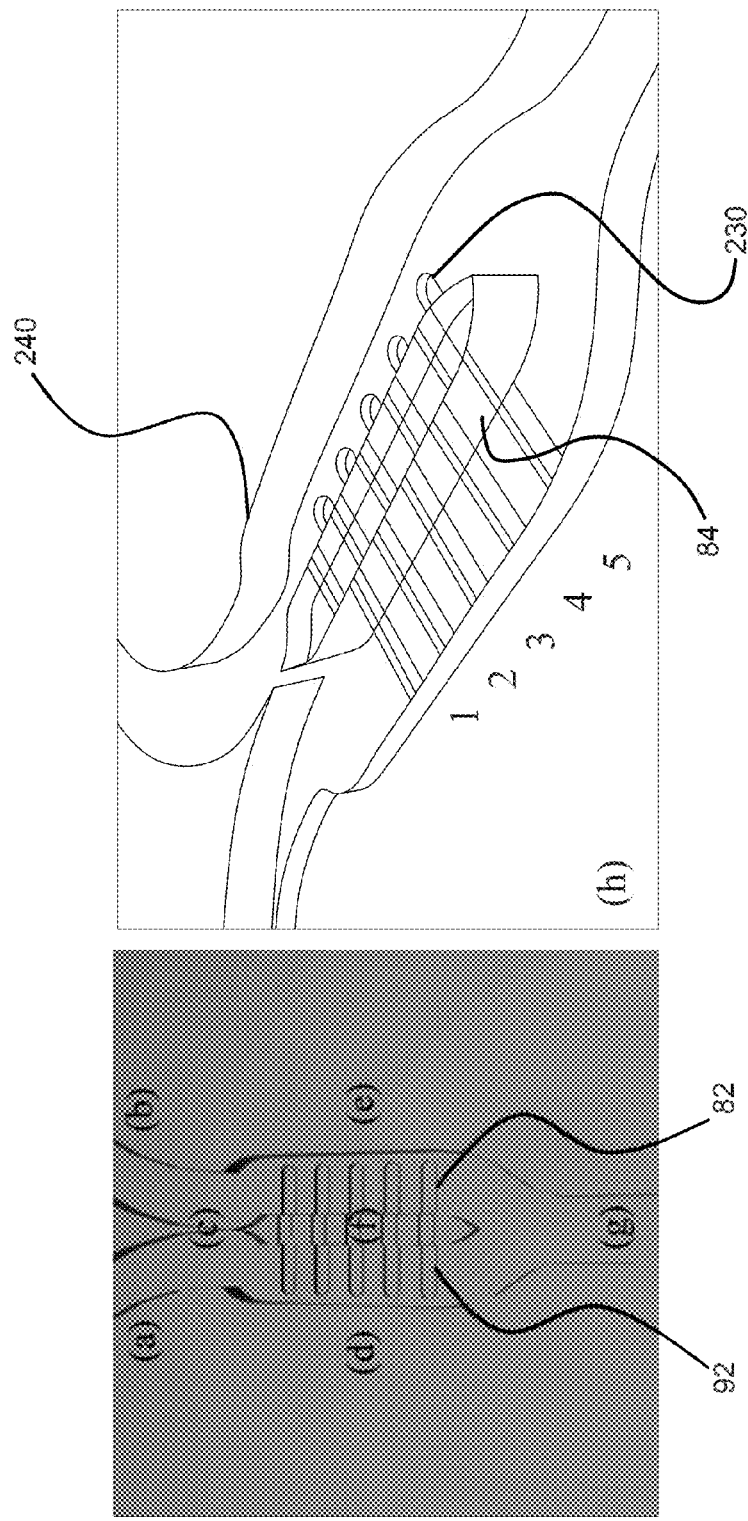
FIG. 2 is a 3D model of a microfluidic gradient generator showing: (a) solution 1 inlet port, (b) solution 2 inlet port, (c) initial intersection point, (d) sink reservoir channel, (e) source reservoir channel, (f) microchannel array, and (g) shared exit port. Isometric view (h) of the microchannel array. The device may have a base plate connected to a top plate, with a plurality of microchannels formed in the bottom plate and the other fluid conduits formed in the top plate so that upon connection an array of microchannels fluidically connect to the source and sink reservoir channels.

The separation section 64 may be used to separate the source reservoir channel 80 from the sink reservoir channel 90. FIG. 1 illustrates a microchannel array 100 comprising a plurality of microchannels 110 that fluidically connect the source 80 and sink 90 reservoir channels. Each microchannel has an inlet end 120 and an outlet end 130, with adjacent channels separated by a separation distance 140. In this example, the microchannel separation distance varies. Referring to FIG. 2, for example, the microchannel separation distance may be constant. The microchannels may be formed through the flow-divider 60 as illustrated in FIG. 1. Alternatively, the microchannels may be formed in a plane that is beneath the flow-divider with the inlets and outlets (120 130) formed in a base plate 230 and the flow-divider and reservoir channels in a top plate 240. This effectively fluidically connects the microchannel inlets and outlets with a bottom surface (82 92) of the source reservoir channel and sink reservoir channel, respectively. Referring to FIGS. 1 and 2, the inlets and outlets optionally are connected to a lumen-facing 84 surface of the reservoir channels.

Figure 8:
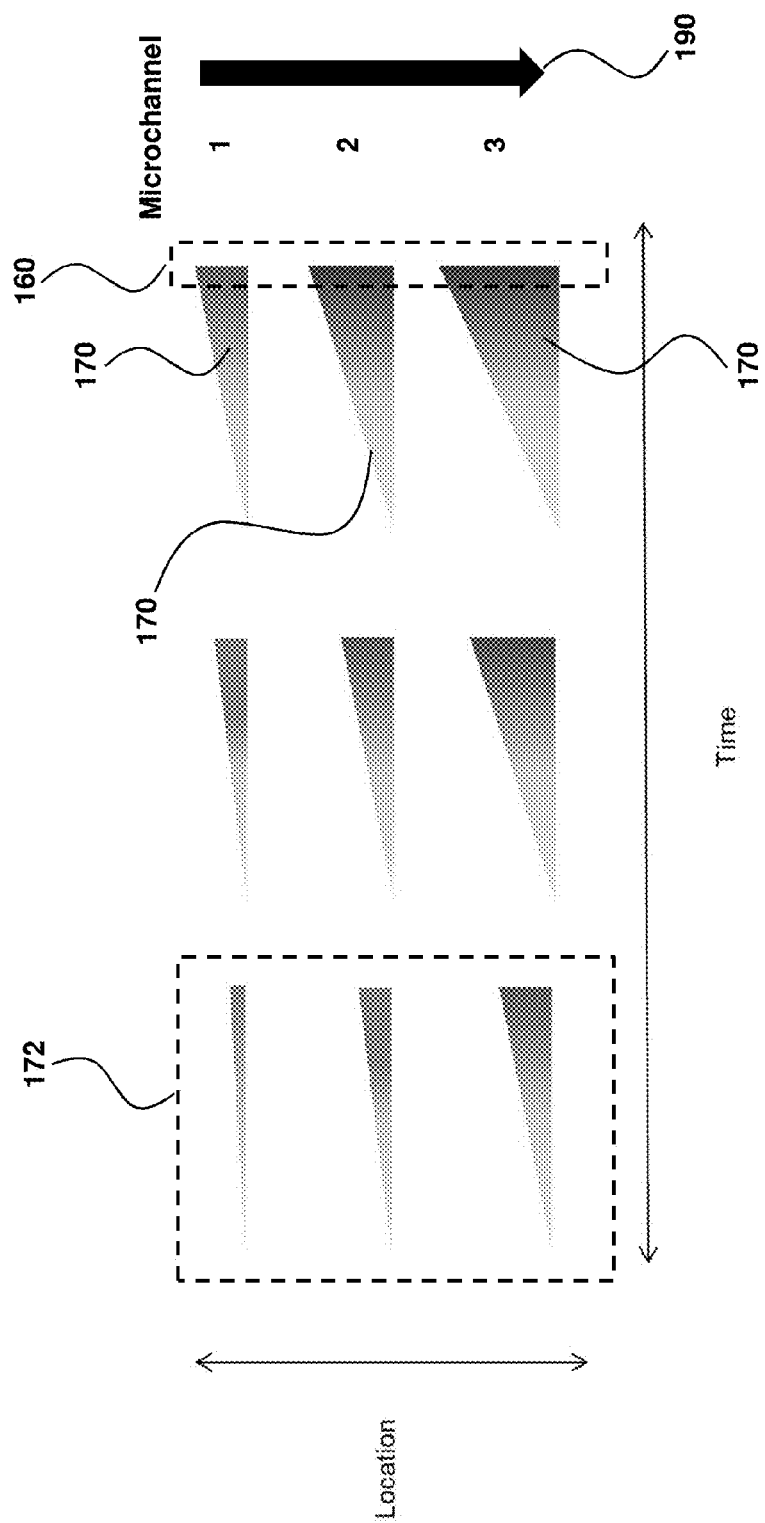
FIG. 8 is a schematic representation of the gradient in each of three microchannels (y-axis) at three different time points x-axis) to illustrate the various gradients generated in the system, including a source reservoir channel gradient, a microfluidic gradient in each of the microchannels, and an array of microfluidic gradients. Positioning of microchannels relative to the axial distance along the source reservoir channel, selection of time, and selection of flow rates provides for tuning dynamic components to achieve desired gradients.

The microchannel array 100 traverses an axial distance 150 along the source reservoir channel. With this configuration, the first fluid flow rate ($Q_1$) 250 and/or the second fluid flow rate ($Q_1$) 260 may be varied by one or two flow-rate controllers (220 222) to obtain a desired fluid flow rate ratio ($Q_1$)/($Q_2$) in the source reservoir channel 80. Under selected flow conditions, such as low Reynolds (Re) flow, a source reservoir channel gradient 160 and an array of microfluidic gradients 170 are established, as schematically illustrated in FIG. 8. FIG. 8 is a simplified illustration showing three microchannels at three different timepoints to illustrate the system's ability to provide spatio-temporal control of the gradients and thereby tune dynamic components of fluid. Each of the nine plots represents a microfluidic gradient 170 in a specific microchannel and at a particular time. At any given time, the plurality of microfluidic gradients 170 (e.g., three in this example) taken together are referred to as an "array of microfluidic gradients" 172. The source reservoir channel gradient 160, refers to the gradient that is provided at the inlet of each of the microchannels and that varies in the direction of mixed fluid flow 190 in the source reservoir channel. For simplicity, the microfluidic gradients shown in FIG. 8 are linear, corresponding to point-source diffusion through the microchannel from the source reservoir channel (having a "maximum" magnitude of the parameter) to the sink reservoir channel (having a "minimum" magnitude of the parameter corresponding to zero). The systems and devices provided herein, however, provide the ability to obtain non-linear microfluidic gradients. Similarly, the source reservoir channel gradient may have a shape by plotting the magnitude of the parameter at the microchannel inlet as a function of location. The source reservoir channel gradient may be linear or non-linear, including exponential or logarithmic in portions or with time. In this manner, high precision may be obtained by placing microchannels close together in regions of the source reservoir channel gradient where the magnitude of the parameter has little variation. Large orders of magnitude, however, may still be addressed in a single experimental set-up by locating microchannels near the start and end of the source channel reservoir gradient where magnitudes at the inlet may be relatively small and large, respectively, depending on flow conditions. The ability to vary gradients with time is further available by changing $Q_1/Q_2$.

Referring to FIG. 1, axial or flow directions of the microchannels, source reservoir channel and microchannels are indicated by arrows 180, 190, and 192, respectively. Optionally, the source and sink reservoir channels join downstream to form an outlet conduit 210. The source and sink reservoir channels may be substantially parallel or parallel to each other over the axial distance 150 and separated by a separation distance 200.

Example 1

Tunable Array of Unique Steady-State Microfluidic Gradients

Provided is an on-chip gradient generator (e.g., microfluidic generator) that has been designed, modelled, fabricated, and characterized, allowing temporal tuning of several unique gradients in parallel for multiple applications. This design allows for steady state programming of the intensities across multiple orders of magnitude while producing exponential, linear, and logarithmic gradient profiles. The magnitude of the gradient intensities is controlled through regulating the ratio of the two on-chip flow inlets ($Q_1/Q_2$) without the need for valves or other active mixers. On-chip binding of biotin by a fluorescent streptavidin complex creates a diffusive barrier that regulates access to the gradient inlets, providing a second orthogonal mechanism for regulating the microgradient intensities. The device is also characterized using an on-chip enzymatic reaction to produce an array of tunable product concentrations within the various microchannels.

Lab-on-a-chip devices have quickly evolved as a means of creating structured microenvironments for various bioassays. One of the chief mechanisms explored for examining on-chip dynamics is the establishment of a concentration gradient of bioactive molecules[1]. This allows for the study of reactions across a wide variety of signal levels to better characterize the response to biochemical cues.[2,3] This methodology has proven useful in several fields, including cancer metastasis,[4,5] stem cell differentiation,[6,7] immune response,[8-11] neural development,[12-13] water toxicity,[14] electrical stimulation,[15,16] and microbial pathology[17-21].

One of earliest microfluidic gradient generators is the simple T junction, where two solutions are brought together at an intersection and as they move down a shared channel the solutes passively diffuse from one solution to another.[22,23] The generated gradient develops as a function of distance from the intersection point, evolving into a sigmoid shape, and eventually reaching uniformity.

A variety of mechanisms have been developed to create steady microfluidic gradients, chief among them convection based gradients,[14,24] and diffusion based gradients.[25,26] A convection-based gradient generator typically works by creating several different concentrations of a biomolecule in separate microchannels, then combining them in a larger shared channel to generate a concentration gradient.[27] By keeping the flow rate in the shared channel relatively high, the time allowed for diffusion is kept low, and thus the established gradient can be kept fairly uniform across the length of the shared channel. A diffusion-based gradient typically works by locating a source and sink on opposite sides of the desired gradient location, with the source supplying the molecule of interest and the sink removing it.[28] Early work in the field made use of finite sources and sinks, such that the established gradient dissipated over time. More recent work has employed microchannels to continually replenish the source and sink concentrations so that the gradient can be maintained indefinitely.

The relative merits of these options have been sufficiently discussed previously,[1] but for this work a diffusion-based gradient is employed for its simplicity of fabrication, stability at low flow rates, and the ease with which many gradients can be assembled in parallel. Convection-based gradient generators have the relative advantage of faster response times, but for most applications a response time on the order of a few minutes is acceptable. Additionally, the high flow rates associated with convection-based gradients are known to displace both secreted cell signaling factors and cells due to increased shear stress.[29] Several modifications have previously been introduced to increase the versatility of these core technologies. This includes the use of valves,[30,31] jets,[3] additional pumps,[32] and hydrogels.[33-36] But in this work these options are avoided to obtain streamlined fabrication and improved ease of use.

One of the primary advantages afforded by the use of a microfluidic architecture is the ability to quickly carry out multiple distinct experiments, and this has been extended to the realm of generating gradients as well.[1] While early work on gradient generation in a microchannel focused on producing a single gradient at a time,[27] this eventually evolved into a basic ladder structure that allows for generation of many identical gradients in parallel.[35] A second key development has been the ability to alter a single gradient within the same device to better mimic the ever changing in vivo microenvironment.[32,37,38] For the most part, work in microgradient generation has remained in one of these two camps, either generating many identical gradients, or dynamically tuning a single gradient. Previous work has been done to produce an array of unique gradients in parallel,[26,39] but those approaches do not allow for the benefit of temporal tuning. Recent work details the production of several identical tunable gradients in parallel for the purpose of carrying out multiple identical experiments.[25] In that work, the tuning consists of simple "on" and "off" switching of a single gradient intensity without the ability to steadily maintain a diverse array of gradient strengths. There exists a need for generating a parallel array of unique microgradients that are temporally tunable to a wide variety of steady state concentrations and that require no additional valves, jets, or other active on-chip mixers.

This example demonstrates the design, modeling, fabrication, and characterization of a temporally tunable array of unique microgradients. The device uses a "smart" geometry that, together with the flow rate and localized chemical interactions, programs the gradient intensity of many microchannels in parallel to generate an array of microfluidic gradients. The ability to simultaneously carry out several distinct experiments allows for the multiplexed study of bioprocesses across varying intensities and time scales for a given biomolecule of interest.

The device has a solution 1 inlet port (IP1), a solution 2 inlet port (IP2), an initial intersection point, a source reservoir channel, a sink reservoir channel, a microchannel array, and a shared exit port, as shown in FIG. 2. The unique dynamically tunable gradient array is accomplished through the employment of two distinct gradients, one that develops along the length of the large source reservoir channel and a second perpendicular set that is generated within the individual members of the microchannel array. The gradient present in the source reservoir channel is analogous to the simple and well characterized T junction gradient generator,[40-42] developing as it migrates away from the intersection point, and it can be temporally adjusted using only the flow rate ratio of the two inlet ports. The flow rate at IP1 ($Q_1$) is significantly higher than that at IP2 ($Q_2$), such that when the two solutions briefly connect at the initial intersection point, solution 1 completely fills the sink reservoir channel and an excess of solution 1 is delivered to the source reservoir channel. As the source reservoir channel continues past the array of the microchannels, solution 2 increasingly breaches the medial shielding flow of solution 1 to reach the microchannel array inlets. This large developing gradient of solution 2 in turn serves as a source for the many individual microchannels, delivering a stable and unique concentration of solution 2 to the inlet of each microchannel. Alternatively, the sink channel on the opposite end of microchannel array is initially homogeneously full of solution 1 and devoid of solution 2.

By providing a brief intersection point between the two large reservoir channels to marginally balance the pressure on each side of the array, and keeping the fluidic resistance of the perpendicular array microchannels several orders of magnitude higher than that of the reservoir channels, bulk fluid flow through the array microchannels is kept to a minimum so that diffusive communication of solution 2 can dominate.[28] The rate of diffusion across the width of the source channel can be finely tuned by the relative flow rates of the two solutions to dictate the fraction of solution 2 that reaches the array. In this manner a unique concentration of solution 2 can be delivered to each of the microchannel array inlets. The flow rate of solution 2 is kept at a constant 3.0 µL/min$^{-1}$, while the flow rate of solution 1 is varied across a range of values. A higher solution 1 flow rate can be used to program a dilute array of microgradients, while a lower solution 1 flow rate can be used to increase the intensity of solution 2 in the microchannel array.

The number of array channels presented is five, but this can be adjusted depending on the demands of the particular application. Additionally, the channels are spaced evenly to produce an approximately linear increase in concentration intensity from one channel to the next, but the spacing can be altered to produce a non-linear gradient at the inlets, such as an exponential or logarithmic distribution. An advantage of the symmetrical design is that should an application require the distribution of surface immobilized biomolecules instead of soluble biomolecules, the flow rate ratios of IP1 and IP2 can be subsequently inverted to generate an opposite overlapping gradient direction across the microchannel array for a second biomolecule of interest.[43]

Figure 3:
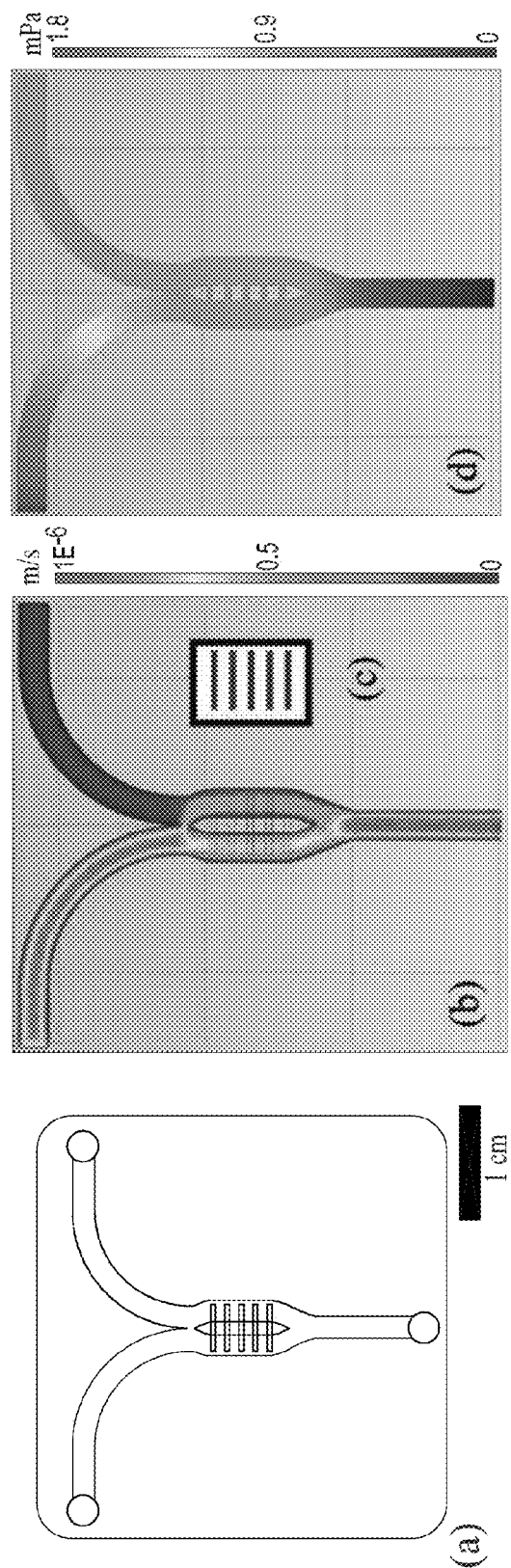
FIG. 3 is an image of (a) fabricated chip and models of (b) the velocity profile in the inlet, source/sink, and outlet channels, (c) an inset of the reduced microchannel array velocity profile at the same scale, (d) the pressure drop across the chip at a 25:3 $\mu L/min^{-1}$ solution 1:solution 2 flow rate ratio.

The chip is formed using a hard plastic to keep it compatible with injection molding and mass production. Initial prototyping was carried out using computer numerically controlled (CNC) machining of a 2 mm thick polycarbonate (PC) base plate and a 0.5 mm thick PC capping film.[44,45] The reservoir channels machined inside the base plate are 1 mm deep and 2 mm wide, while the individual microgradient array channels fabricated within the capping film are 0.15 mm deep, 0.4 mm wide, and 1 mm long. Following CNC machining and a brief deburring process, the two sides of the chip are bound using an adhesive, such as a double sided pressure sensitive adhesive (Adhesives Research).[46] Because the CNC machining is used, the device surface can be left quite rough by the machining tools. This did not produce a notable effect on mixing performance, but did result in increased back pressure when 0.1% BSA was used in the buffer solutions as more bubbles were generated. The completed device is shown in FIG. 3A. The simplicity of the design ensures that the device can be reproduced across a wide variety of substrate types depending on the application. PEEK™ tubing (Idex) is inserted into the device that interfaces tightly with silicone tubing (Dow Corning) connected to two syringe pumps (New Era Pump Systems) that are controlled via LabVIEW® software (National Instruments).

Experimental validation of the device is in three stages. First, the device is filled with water and fluorescein isothyocyanate (FITC) to demonstrate the establishment of several unique parallel gradients. Second, the device is filled with Cy3-labeled streptavidin and the second input is varied between buffer solution and buffer solution containing biotin to determine the effect of flow rate and a noncovalent molecular interaction,[47] on the diffusion-based gradient profile within the microchannel array. Finally, alkaline phosphatase (AP) activity is observed on the device to validate its suitability for producing unique and tunable microfluidic gradients of on-chip generated enzymatic product, including an array of microfluidic gradients.

Characterization with FITC: To visualize simple chemical gradients, IP1 is filled with pure water (Biotechnology Performance Certified (BPC), Sigma-Aldrich W3513) and IP2 filled with a solution of 10 µM FITC in BPC water. The FITC solution is introduced at a constant 3 µL/min$^{-1}$, while the pure water solution is programmed via LabVIEW with flow rates between 15 and 65 µL/min$^{-1}$. The elevated flow rate of the pure water solution produces a medial shielding flow in the source reservoir channel that FITC must diffuse through to reach the microchannel array inlets, and this results in unique gradient intensities within each member of the array (e.g., unique microfluidic gradients that form the array of microfluidic gradients). For detection, a FITC filter set (Semrock Brightline FITC-3540B) is used with 2× (Nikon Plan Achromat UW, Nikon, NA=0.06, WD=7.5 mm) and 10× (Modulation Optics, Inc., ELWD Plan Fluor, NA=0.30) microscope objectives and a 512×512 pixels electron-multiplying charge coupled device (EM-CCD, Andor iXon DV887ECS) cooled down to −20° C. with exposition times of 0.2 s. Additional neutral density (ND) filtering prevents saturation of the CCD when needed. The unique gradient intensities are steady over time for a given flow rate ratio. To determine the stability of the generated gradients over time, each microchannel is examined at higher magnification over 30 min under a fixed flow rate ratio of 60:3 µL/min$^{-1}$.

Streptavidin-Biotin imaging: Device characterization further includes studying the effect of a noncovalent on-chip molecular interaction on the generated gradient intensity. A solution of 0.25 mg/mL$^{-1}$ streptavidin-Cy3 (Sigma-Aldrich S6402, 4.8 Cy3/molecule) in 50 mM Tris, pH=8 with 0.1% bovine serum albumin (BSA, Fraction V, Fatty-acid free, Calbiochem 126575) is flowed into IP2 of the device at a constant rate of 3 µL/min$^{-1}$. The IP2 flow rate is varied between 15 and 65 4/min$^{-1}$ containing, first 50 mM Tris at pH=8, then 10 µM biotin (Pierce Biotechnology, Inc. 29129) in 50 mM Tris at pH=8 to assess the effect of binding on the gradient generation. From simulation results, it is predicted that the complexation reaction results in an increased diffusive barrier, leading to detectably lower levels of streptavidin reaching the microchannel array inlets, and thus lower gradient intensities. The microchannel array portion of the device is imaged using a Cy3 filter set (Semrock Brightline Cy3-4040B) with a 2× objective on an EM-CCD with an exposition of 1.0 s and cooled to −20° C. Additionally, each individual channel is imaged with a 10× objective (Modulation Optics, Inc., ELWD Plan Fluor, NA=0.30) to observe the gradient profile in a single microchannel with higher sensitivity.

AP activity visualization: Lyophilized AP (EC 3.1.3.1, from porcine kidney, Sigma-Aldrich P4439) is re-suspended in 50 mM Tris-HCl, pH=8.01 (adjusted with a pH meter (Acorn ph6) calibrated with NIST standard solutions) at a concentration of 0.5 unit/mL. 9H-(1,3-Dichloro-9,9-dimethylacridin-2-one-7-yl) phosphate (DDAOP, diammonium salt, Life Technologies D6487) is a known substrate of AP,[48] and emits a fluorescence signal ($\lambda_{me}$=460 nm, $\lambda_{me}$=610 nm) that can be imaged using a Nikon Ti—U inverted microscope with a mercury light source (Intensilight C-HGFI) filtered using a Cy3 filter set. The dephosphorylation product (DDAO) also emits a red fluorescence ($\lambda_{me}$=660 nm), but absorbs with a maximum almost 200 nm apart from DDAOP ($\lambda_{me}$=645 nm). It is therefore possible to detect the product, DDAO, independently from the substrate using a Cy5 filter set (Nikon Cy5 HYQ) with very minimal filter crosstalk. IP1 is fed 50 µM DDAOP in 50 mM Tris-HCl, pH=8.01 at flow rates between 15 and 50 µL/min$^{-1}$, whereas IP2 is fed 0.5 unit/mL AP in 50 mM Tris-HCl, pH=8.01 with 0.1% w/v BSA at a rate of 3 µL/min$^{-1}$. DDAOP thus fills the entire sink reservoir channel, and provides a shielding flow in the source reservoir channel. As AP gradually moves down the source reservoir channel and diffuses through the shielding flow of DDAOP, it produces an evolving concentration of DDAO detected in the microchannel array. The Cy3 and Cy5 filter sets are used with 2× and 10× objectives of an inverted microscope equipped with a EM-CCD operated at exposures of 1 s and cooled down to −20° C.

Modeling: Comsol™ Multiphysics is used to model the three dimensional fluid flow, diffusion paths, and binding events. Comsol is selected from among several possible software packages because of the fluidity with which its microfluidic module can be integrated with other physics. The device is modeled using incompressible Newtonian fluid in single-phase laminar flow with no-slip boundary conditions to establish steady diffusion-based gradients. This involves simultaneously solving for the Reynolds number (1), Peclet number (2), Navier-Stokes (3), species transport (4), and continuity equations (5):

$$Re = \frac{\rho u L}{\mu} \quad (1)$$

$$Pe = \frac{uL}{D} \quad (2)$$

$$\frac{\delta u}{\delta t} + (u \cdot \nabla) u = -\nabla p + \frac{1}{Re} \nabla^2 u \quad (3)$$

$$\frac{\delta \theta}{\delta t} + u \cdot \nabla \theta = \frac{1}{Pe} \nabla^2 \theta \quad (4)$$

$$\nabla \cdot u = 0 \quad (5)$$

where Re is the Reynold's number, ρ is the density, u is the velocity vector, L is the characteristic linear dimension, Pe is the Peclet number, D is the diffusion coefficient, t is the time, p is the pressure, Re is the Reynolds number, and θ is the normalized concentration density.[49]

The device geometry is created in COMSOL and the physical properties of the fluid inserted as follows. The viscosity of the solution is set to 1 mPa s, and the density to 1 g/cm$^{-3}$. The diffusion coefficient of biotin is set to 6×10$^{-10}$ m$^2$/s$^{-1}$, DDAO/P is set to 5×10$^{-10}$ m$^2$/s$^{-1}$, AP is set to 6×10$^{-11}$ m$^2$/s$^{-1}$, and streptavidin is set to 7×10$^{-11}$ m$^2$/s$^{-1}$. Streptavidin is modeled as reacting with 4 biotin molecules to produce a higher molecular weight streptavidin-biotin cluster. AP is modeled as converting DDAOP to DDAO in a one-to-one reaction.

Results and Discussion. Modeling. The typical inlet velocities used are 15-65 µL/min$^{-1}$ for IP1 and 3 µL/min$^{-1}$ for IP2. Using a volumetric flow rate ratio of 25:3 µL/min$^{-1}$, typical flow rates of 300 μm/s$^{-1}$ are modeled in the large 1 mm tall reservoir channels, while a lower flow rate of 2.2 μm/s is found in the smaller 0.15 mm tall array microchannels, as shown in FIGS. 3B and 3C. Pressure drop across the device is found to be approximately 1.7 mPa from IP1 to the shared outlet, and 0.7 mPa from IP2 to the shared outlet, as shown in FIG. 3D. Using the simulated flow rate, density, viscosity, characteristic length, and diffusion coefficient, the Peclet number and Reynolds number are calculated for the two channel types. For the reservoir channels the Peclet number is approximately $4.3 \times 10^7$, while the Reynolds number is approximately 0.6. For the array microchannels the Peclet number is approximately 4.3, while the Reynolds number is approximately $3 \times 10^{-4}$. Within the array microchannels the flow is primarily laminar and at low flow rates molecular motion is diffusion dominant.

Figure 4:
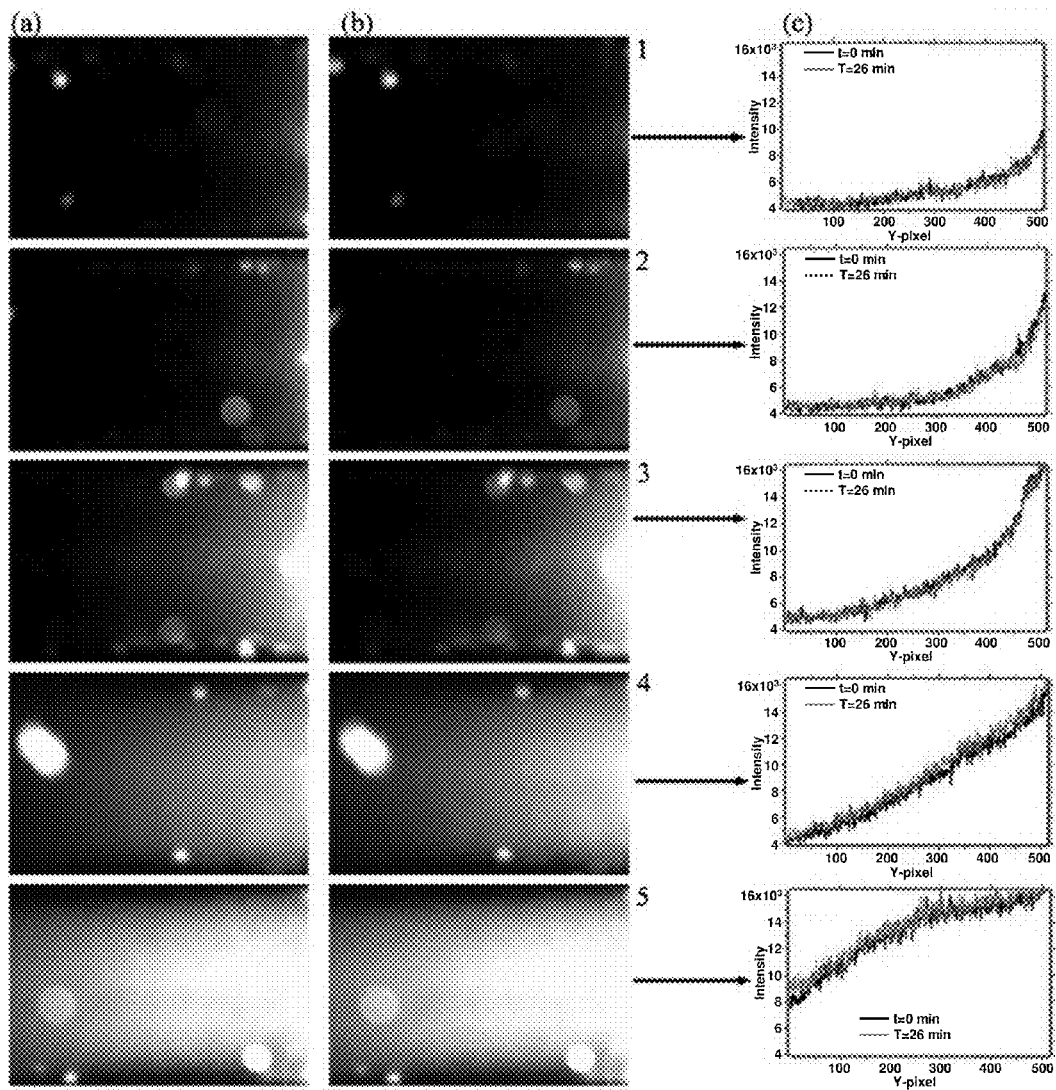
FIG. 4: Stability of the unique microgradient array obtained with water delivered to IP1 at a flow rate of 60 $\mu L/min^{-1}$ and 100 FITC delivered to IP2 at a flow rate of 3 $\mu L/min^{-1}$ (a) as initially established in the microchannel array after 20 minutes of flow and (b) 26 min later at the same flow rate. Graphical representation of (c) the intensity along each microchannel (Y axis) as a function of the position within each 1 mm long channel (X axis). The fluorescent intensity is recorded along the channel center line designated by the black arrow location, and the data is presented for the initial measurement (black trace) and a second measurement 26 minutes later (grey trace).

Experimental Validation. Stability of the gradients generated. The five individual gradients are detectable within 5 min of programming the inlet flow rates, and steady with 20 min. Additionally the gradient intensity is characterized over 26 minutes with the flow rates held constant at 3 μL/min$^{-1}$ for the FITC solution and 60 μL/min$^{-1}$ for the water, as shown in FIG. 4. The signal is binned horizontally (X-axis) from the 400 columns of pixels defining the channel with 10× magnification initially and after 26 min. In each microchannel, the obtained binned intensity trace along the gradient (Y axis) after 26 minutes is subtracted from and normalized by the initial one, point by point. The absolute average deviation (AAD) from the mean is calculated. For each channel, the difference in signal after 26 min is listed in Table 1.

TABLE 1

AAD variation as a function of channel number

| | Microchannel | | | | |
|---|---|---|---|---|---|
| | 1 | 2 | 3 | 4 | 5 |
| AAD: | 3.0% | 1.9% | 1.3% | 1.4% | 1.7% |

Most of the difference arises from the difficulty to align each channel with the field of view for each set of measurements. But essentially, there is less than 2% variation in the fluorescence intensity 26 minutes after the unique gradients have been established. Plots of the intensity as a function of position for both measurement set are presented in FIG. 4C, as a slice along the path of the black arrow, with the initial data set plotted in black and the second data set plotted in grey.

Figure 5:
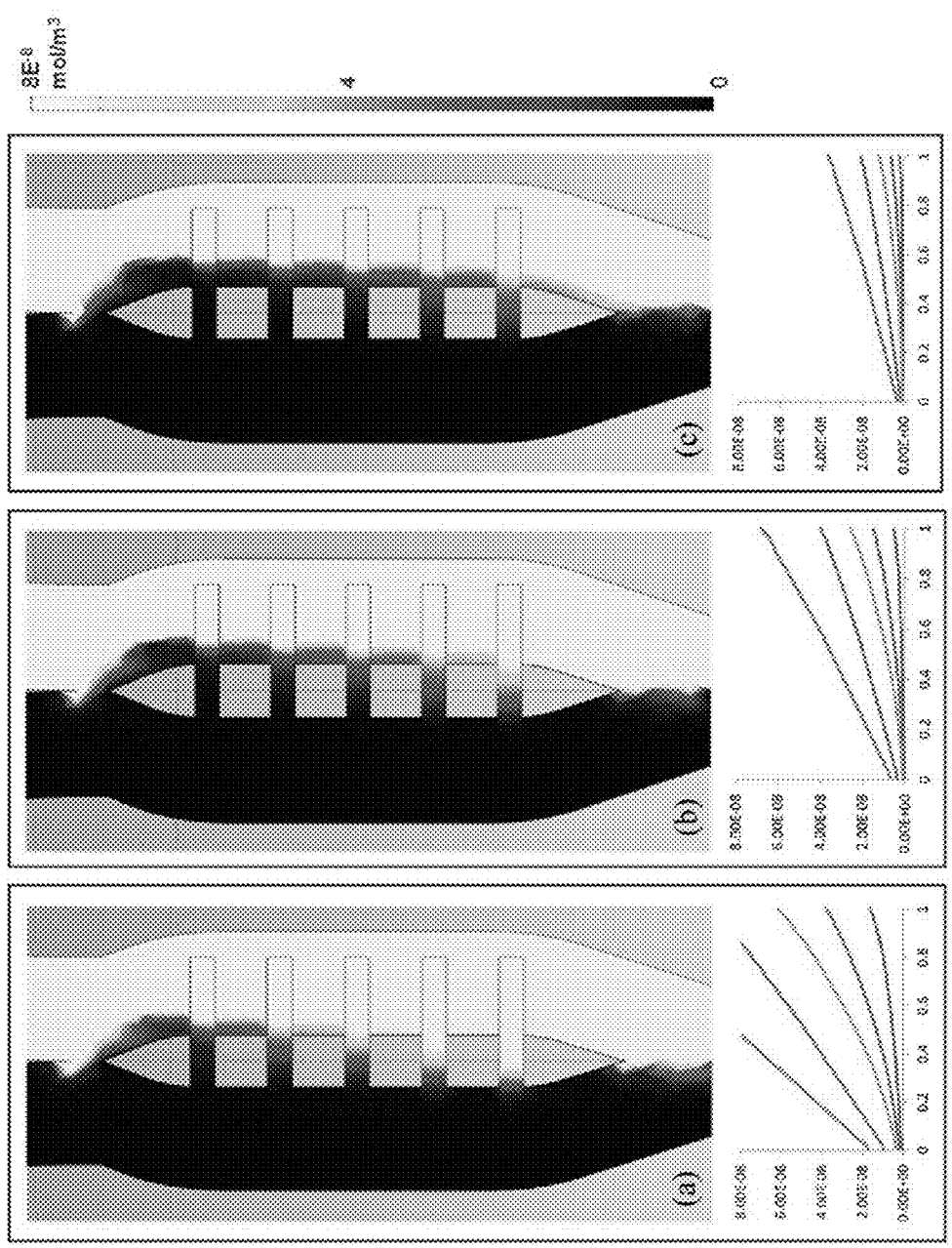
FIG. 5: Model of the steady state tuning of streptavidin gradients in the microchannel array in the absence biotin as a function of three different flow rates, with associated graphs of the streptavidin intensity: (a) 45:3 $\mu L/min^{-1}$, (b) 50:3 $\mu L/min^{-1}$, and (c) 55:3 $\mu L/min^{-1}$. The scale is set to the maximum in-microchannel value for the middle 50:3 $\mu L/min^{-1}$ simulation.

The increase in variation for the first channel can also be attributed to the increased pressure difference and turbulence at the initial intersection point within the chip. Beyond contributing to run to run variation, the various pressure differences across the microchannel array (lowest in the microchannel closest to the shared outlet) also affect the shape of the generated gradients. Initial modeling work predicts exponential curves in the channels closest to the initial intersection point and linear gradients in the channels closest to the shared outlet, as shown in FIG. 5. It is theorized that this is a result of the balancing act taking place between bulk fluid flow and molecular diffusion. With a higher pressure differential across the earlier channels, increased bulk fluid flow from the sink channel to the source channel is expected. This limits the distance biomolecules can diffuse from the source channel to the sink channel, resulting in exponential concentration profiles. Looking at channels nearer to the shared outlet, the pressure differential across them is less, thus leading to reduced bulk fluid flow from the sink to source channels, allowing more diffusive communication of biomolecules from the source channel to the sink channel, and creating linear concentration profiles. Experimental results confirm this transition from exponential to linear microgradients. The results from channel 5 even produce an unexpected transition from linear to logarithmic gradient profiles. Overall, the device is able to reliably produce several different microfluidic gradient intensities with unique gradient profiles.

Biotin-streptavidin diffusion barrier. Multiple unique microfluidic gradients are established in a single microchannel array. Via simulation, the intensity of unique streptavidin gradients is shown to vary as a function of both the volumetric flow rate ratio and the presence or absence of biotin. Flow rates of 45, 50, and 55 μL/min$^{-1}$ are presented, with increasing flow rates for the solution 1 inlet port corresponding to decreased gradient intensities (FIG. 5). Additionally, the inclusion of biotin in the solution 1 inlet port results in a significant decrease in the streptavidin gradient intensities, as shown in FIGS. 6A and 6B.

Figure 6:
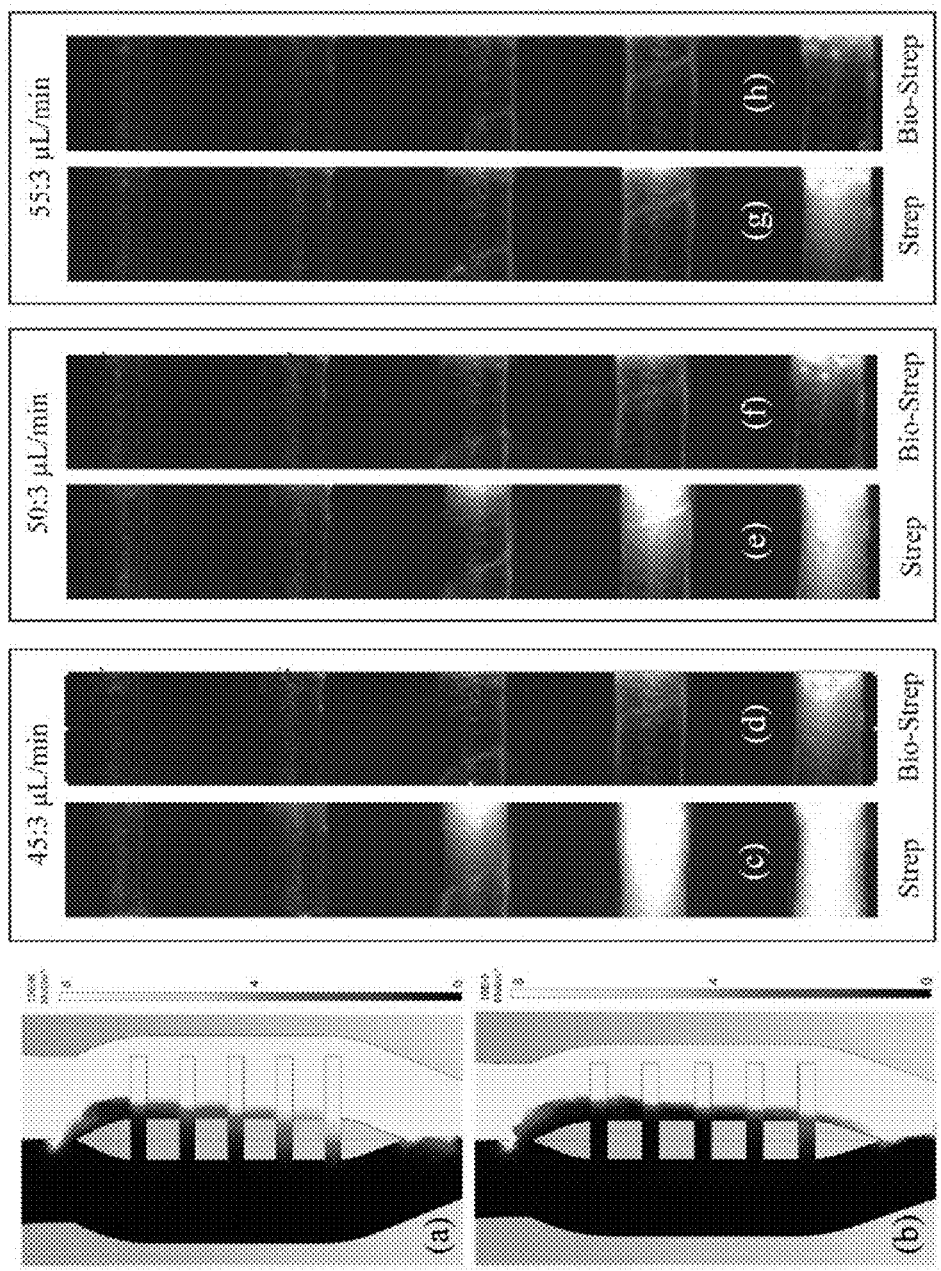
FIG. 6: Model of (a) the evolving on-chip streptavidin concentration profile in the absence of biotin with a 50:3 buffer to streptavidin flow rate, with the scale adjusted to the maximum in-microchannel value, and (b) the evolving on-chip streptavidin concentration profile in the presence of biotin with a 50:3 biotin to streptavidin flow rate, with the same scale. Fluorescent images at 2× magnification of unique streptavidin gradients in the microchannel array at a (c) 45:3 $\mu L/min^{-1}$ flow rate ratio in the absence of biotin, (d) 45:3 $\mu L/min^{-1}$ flow rate ratio in the presence of biotin, (e) 50:3 $\mu L/min^{-1}$ flow rate ratio in the absence of biotin, (f) 50:3 $\mu L/min$ flow rate ratio in the presence of biotin, (g) 55:3 $\mu L/min^{-1}$ flow rate ratio in the absence of biotin, and (h) 55:3 $\mu L/min^{-1}$ flow rate ratio in the presence of biotin.

Experimentally, IP1 is initially connected to a syringe pump containing pH=8 Tris buffer, while the Cy-3 labeled streptavidin is prepared at a final concentration of 4.2 μM and pumped into IP2. The streptavidin-Cy3 solution is held at a constant flow rate of 3 μL/min$^{-1}$ whereas the flow rate of the buffer solution is adjusted from 45 to 50 to 55 μL/min$^{-1}$. This brings the streptavidin-Cy3 concentration to 0.26, 0.24, and 0.22 nM, respectively, and establishes 3 different sets of unique streptavidin gradients in the microchannel array (FIG. 6). Subsequently, the device is flushed with buffer at a high flow rate (>500 μL/min$^{-1}$) until no residual fluorescence is seen in the microchannels. The IP1 solution is switched to a 10 μM biotin solution in the same Tris buffer, with the same cycle of flow rates from 45 to 50 to 55 μL/min$^{-1}$, producing effective concentrations of 9.3, 9.4, and 9.5 μM, respectively. This results in much weaker individual gradients of fluorescent streptavidin in the microchannel array.

The concentration ratio of biotin to streptavidin is at least 36. This ensures a rapid saturation of the four biotin-binding sites on the streptavidin,[50] and total irreversible complexation of free streptavidin in the buffer conditions used. The quantitative molecular interaction between biotin and streptavidin creates an increased diffusive barrier for streptavidin migration into the microchannel array. The individual gradients in each microchannel at 55 μL/min$^{-1}$ of Tris buffer overlap well with the gradients at 45 μL/min$^{-1}$ of Tris buffer with biotin (FIG. 6), showing that similar gradient intensities can be reached regardless of the on-chip molecular interactions taking place. The increase in flow rate of 10 μL/min$^{-1}$ empirically characterizes the additional diffusive barrier that must be overcome when biotin is introduced into the system.

This demonstrates that the molecular interaction between biotin and streptavidin results in an increased diffusive barrier for the migrating streptavidin molecules compared to the pathway through simple buffer. COMSOL simulations show that the gradient profile is affected when the diffusion coefficient changes by a factor 2. However, the binding of up to four biotin molecules to the streptavidin only increases the molecular weight of the complex by about 980 g mol$^{-1}$, i.e. only 1.6% of the overall molecular weight of the streptavidin-biotin complex. This guarantees negligible variations to the diffusion coefficient. Therefore, the evolution of the gradient profile illustrated in FIG. 6 can be mostly attributed to the irreversible complexation event occurring in the gradient mixer device. This demonstrates manipulation of steady state on-chip gradient generation using localized molecular interactions in a geometry that is compatible with additional molecules beyond simple gaseous species.[51]

On-chip enzymatic product generation. An array of unique gradients of DDAO, generated on-chip by controlling the enzymatic reaction between AP and DDAOP, is demonstrated. The intensity of the parallel gradients can be dynamically tuned by altering the flow rates of the substrate and product. This on-chip enzymatic reaction is modeled for multiple flow rates, with the associated DDAOP and DDAO concentrations shown in (FIG. 7A-7D). The de-phosphorylation of DDAOP by AP results in an increasing amount of DDAO in the source reservoir channel proportional to the distance from the initial intersection point, supplying a unique concentration of DDAO to each of the microchannel array inlets. This results in minor gradient generation in the first one or two microchannels, and much higher gradients in the last few microchannels.

Figure 7:
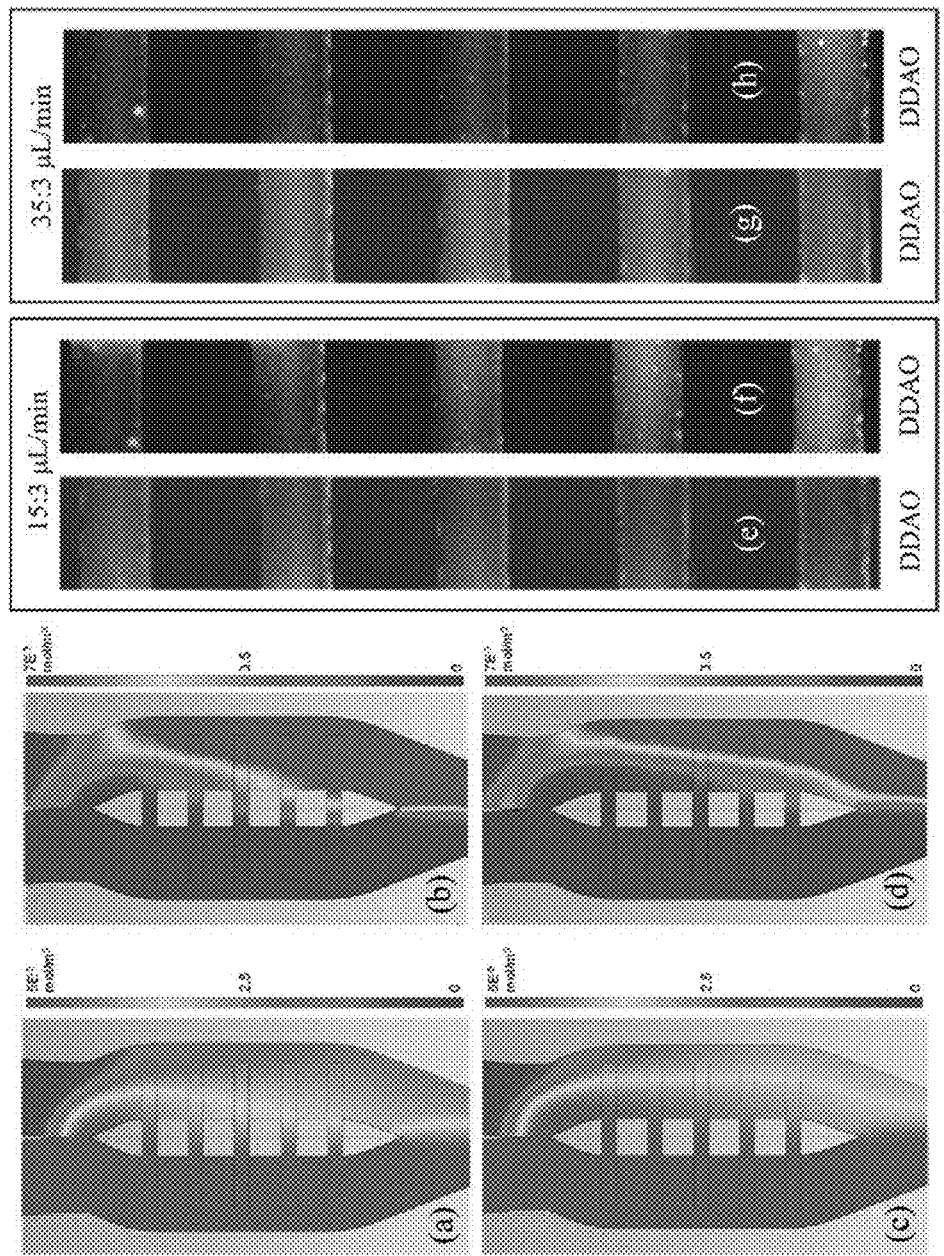
FIG. 7: Model of an on-chip AP-DDAOP reaction using a 15:3 $\mu L/min^{-1}$ 50 $\mu M$ DDAOP to 13.4 $\mu M$ AP flow rate ratio with (a) DDAOP (substrate) concentration and (b) DDAO (product) concentration. Model of an on-chip AP-DDAOP reaction using a 35:3 $\mu L/min^{-1}$ 50 $\mu M$ DDAOP to 13.4 $\mu M$ AP flow rate ratio with (c) DDAOP concentration and (d) DDAO concentration. For all DDAOP values the maximum scale is set to the initial 50 $\mu M$ input concentration, while for the DDAO values the scale is adjusted to the maximum in-microchannel value. Fluorescent images at 2× magnification of an on-chip AP-DDAOP reaction using a 15:3 $\mu L/min^{-1}$ 50 $\mu M$ DDAOP to 13.4 $\mu M$ AP flow rate ratio with (e) DDAOP concentration and (f) DDAO concentration. Fluorescent images at 2× magnification of an on-chip AP-DDAOP reaction using a 35:3 $\mu L/min^{-1}$ 50 $\mu M$ DDAOP to 13.4 $\mu M$ AP flow rate ratio with (g) DDAOP concentration and (h) DDAO concentration.

Experimentally, tuning of the on-chip DDAO generation is realized by gradually decreasing the flow rate of a solution of 50 µM DDAOP in Tris buffer at pH=8 from 45 to 15 µL/min$^{-1}$ while a buffered solution of enzyme (0.5 units/mL or 15.4 µM) is kept at a flow rate of 3 µL/min$^{-1}$ (FIG. 7B). At an initial flow rate ratio of 45:3 µL/min$^{-1}$, high levels of the substrate DDAOP are detected uniformly in all five microchannels and the amount of the enzymatic product DDAO is too low to be resolved within the microchannel array.

As the flow rate of the substrate solution decreases to 35 µL/min$^{-1}$, gradients of enzymatic product are established in each microchannel. Initially, only the last two microchannels show a strong enough level of product to be detected (FIG. 7H). These lower channels steadily increase in intensity as the IP1 flow rate decreases to 25 µL/min$^{-1}$. When the DDAOP flow rate eventually decreases to 15 µL/min$^{-1}$, all five members of the microchannel array display a measurable unique gradient of the enzymatic product DDAO (FIG. 7F). The signal detection in each microchannel is proportional to the distance from the initial intersection point. Correspondingly, at this high level of DDAO generation an inverse gradient of DDAOP product can be detected in the microchannel array (FIG. 7E). At a flow rate of 15 µL/min$^{-1}$ for the 50 µM substrate concentration (41.6 µM effective concentration) and 3 µL/min$^{-1}$ for the 15.4 µM enzyme solution (2.6 µM effective concentration), enough DDAOP can be converted to detect a significant decrease in the fluorescence of the substrate remaining in each microchannel.

The delivery of product into microchannels with a tunable concentration profile from 2 components using an on-chip manipulation has application when local delivery to an established population of biomolecules or cells within the microchannel array is needed.

Demonstrated herein is a microgradient generator that is capable of producing an array of unique gradients that can be temporally tuned to a broad continuum of reliable steady state values through the simple adjustment of the flow rate ratio of the two input solutions. This is accomplished without the need for on-chip actuators, sensors, valves, jets, membranes, hydrogels and/or complex geometrical configurations.

The stability of the device over time is shown to be uniformly high, varying by less than 2% over 26 minutes of continuous operation. The response of the microgradient intensities to changes in the flow rate ratio of the two chip inputs is shown, with a higher disparity in two flow rates strongly and reliably correlating with a decreased gradient intensity. Additionally on-chip binding of streptavidin to biotin is shown to alter the gradient strength by creating an additional diffusive barrier within the chip. Finally, on-chip generation of various unique DDAO concentration gradients demonstrates using uniquely tunable concentrations of the enzyme AP and its associated substrate DDAOP.

The device is used to generate gradients across a broad spectrum of intensities and applications, providing a tunable steady state platform that is no longer tied to its initial starting concentrations. This platform technology can be useful for a variety of applications requiring highly flexible tuning of unique biomolecular gradients. For instance, the devices and methods presented herein are suitable for a tumor cell culture in the presence of a rapidly evolving growth factor continuum to determine the effect on cell growth and migration. Another application is examining the response of tumor cells to a gradient of a cancer reducing agent. Examples of various applications are summarized in TABLE 2.

TABLE 2

Summary of Applications

| Application | Fluid 1 | Fluid 2 | Microchannel | Gradient |
| --- | --- | --- | --- | --- |
| Toxicity | Saline | Saline + drug | Cultured Cells | [drug] |
| Cancer drug screen | Saline | Saline + drug | Cultured tumor cells or biological fluid (e.g., blood, urine, saliva) | [drug candidate] |
| Chemotaxis | Saline | Saline + chemotactic agent | Immune cell | [chemotactic agent] |
| Surface Treatment | Fluid | Fluid + chemical | Microchannel surface (lumen) In situ microbead coating | [chemical] adsorbed to microchannel lumen or microbead; frictional enhancing compound; adhesive; light reflecting materials; hydrophobic/philic treatment compound |
| Polymerization | Fluid | Fluid + prepolymer | Polymerization signal | Degree of polymerization |
| Electroconductivity | Fluid | Fluid + electrolyte | Electric Potential | [electrolyte] |
| Chemical Reaction | Fluid + catalyst | Fluid + reactant(s) | — | [product] of chemical reaction |
| Temperature | Fluid at T1 | Fluid at T2 | — | Temperature |
| Amplification via PCR | Fluid + PCR reagents | Polynucleotide and/or target probe | Amplified product | [amplified product] |

TABLE 2-continued

Summary of Applications

| Application | Fluid 1 | Fluid 2 | Microchannel | Gradient |
|---|---|---|---|---|
| Biological response | Saline | Saline + agent | Cultured Cells or biological fluid (e.g. effusions, ascites, blood, serum, plasma, urine, saliva) | [agent]; response to environmental exposure (e.g. radiation, pollutant, stimulating agent |

REFERENCES

1 S. Kim, H. J. Kim and N. L. Jeon, Integr. Biol., 2010, 2, 584-603.
2 B. M. Baker and C. S. Chen, J. Cell Sci., 2012, 125, 3015-3024.
3 T. M. Keenan and A. Folch, Lab Chip, 2008, 8, 34-57.
4 Y. Alsayed, H. Ngo, J. Runnels, X. Leleu, U. K. Singha, C. M. Pitsillides, J. A. Spencer, T. Kimlinger, J. M. Ghobrial, X. Jia, G. Lu, M. Timm, A. Kumar, D. Cote, I. Veilleux, K. E. Hedin, G. D. Roodman, T. E. Witzing, A. L. Kung, T. Hideshima, K. C. Anderson, C. P. Lin and I. M. Ghobrial, Blood, 2007, 109, 2708-2717.
5 S. Fujii, M. Uematsu, S. Yabuki, M. Abo, E. Yoshimura and K. Sato, Anal. Sci., 2006, 22, 87-90.
6 B. G. Chung, L. A. Flanagan, S. W. Rhee, P. H. Schwartz, A. P. Lee, E. S. Monuki and N. L. Jeon, Lab Chip, 2005, 5, 401-406.
7 O. C. Amadi, M. L. Steinhauser, Y. Nishi, S. Chung, R. D. Kamm, A. P. McMahon and R. T. Lee, Biomed. Microdevices, 2010, 12, 1027-1041.
8 V. V. Abhyankar, M. A. Lokuta, A. Huttenlocher and D. J. Beebe, Lab Chip, 2006, 6, 389-393.
9 F. Lin and E. C. Butcher, Lab Chip, 2006, 6, 1462-1469.
10 N. L. Jeon, H. Baskaran, S. K. W. Dertinger, G. M. Whitesides, L. Van De Water and M. Toner, Nat. Biotechnol., 2002, 20, 826-830.
11 D. Kim, M. A. Lokuta, A. Huttenlocher and D. J. Beebe, Lab Chip, 2009, 9, 1797-1800.
12 H. Song, G. Ming and M. Poo, Nature, 1997, 388, 275-279.
13 S. K. W. Dertinger, X. Jiang, Z. Li, V. N. Murthy and G. M. Whitesides, Proc. Natl. Acid. Sci. U.S.A., 2002, 99, 12542-12547.
14 T. Glawdel, C. Elbuken, L. E. J. Lee and C. L. Ren, Lab Chip, 2009, 9, 3243-3250.
15 J. Li and F. Lin, Trends Cell Biol., 2011, 21, 489-497.
16 J. Li, L. Zhu, M. Zhang and F. Lin, Biomicrofluidics, 2012, 6, 024121.
17 H. Mao, P. S. Cremer and M. D. Manson, Proc. Natl. Acid. Sci. U.S.A., 2003, 100, 5449-5454.
18 J. Atencia, J. Morrow and L. E. Locascio, Lab Chip, 2009, 9, 2707-2714.
19 T. Ahmed, T. S. Shimzu and R. Stocker, Nano Lett., 2010, 10, 3379-3385.
20 T. I. Moore, C.-S. Chou, Q. Nie, N. L. Jeon and T.-M. Yi, PLoS One, 2008, 3, e3865.
21 M.-E. Brett, R. DeFlorio, D. E. Stone and D. T. Eddington, Lab Chip, 2012, 12, 3127-3134.
22 A. E. Kamholz, B. H. Weigl, B. A. Finlayson and P. Yager, Anal. Chem., 1999, 71, 5340-5347.
23 A. Hatch, A. E. Kamholz, K. R. Hawkins, M. S. Munson, E. A. Schilling, B. H. Weigl and P. Yager, Nat. Biotechnol., 2001, 19, 461-465.
24 J. J. VanDersarl, A. M. Xu and N. A. Melosh, Lab Chip, 2011, 11, 3057-3063.
25 J. Atencia, G. A. Cooksey and L. E. Locascio, Lab Chip, 2012, 12, 309-316.
26 B. Mosadegh, C. Huang, J. W. Park, H. S. Shin, B. G. Chung, S.-K. Hwang, K.-H. Lee, H. J. Kim, J. Brody and N. L. Jeon, Langmuir, 2007, 23, 10910-10912.
27 N. L. Jeon, S. K. W. Dertinger, D. T. Chiu, I. S. Choi, A. D. Stroock and G. M. Whitesides, Langmuir, 2000, 16, 8311-8316.
28 A. Shamloo, N. Ma, M. Poo, L. L. Sohn and S. C. Heilshorn, Lab Chip, 2008, 8, 1292-1299.
29 G. M. Walker, J. Sai, A. Richmond, M. Stremler, C. Y. Chung and J. P. Wikswo, Lab Chip, 2005, 5, 611-618.
30 C.-H. Hsu and A. Folch, Appl. Phys. Lett., 2006, 89, 144102.
31 D. Irimia, D. A. Geba and M. Toner, Anal. Chem., 2006, 78, 3472-3477.
32 Y. Liu, J. Sai, A. Richmond and J. P. Wilkswo, Biomed. Microdevices, 2008, 10, 499-507.
33 N. Zaari, P. Rajagopalan, S. K. Kim, A. J. Engler and J. Y. Wong, Adv. Mater., 2004, 16, 2133-2137.
34 S.-Y. Cheng, S. Heilman, M. Wasserman, S. Archer, M. L. Shuler and M. Wu, Lab Chip, 2007, 7, 763-769.
35 W. Saadi, S. W. Rhee, F. Lin, B. Vahidi, B. G. Chung and N. L. Jeon, Biomed. Microdevices, 2007, 9, 627-635.
36 H. Wu, B. Huang and R. N. Zare, J. Am. Chem. Soc., 2006, 128, 4194-4195.
37 D. Amarie, J. A. Glazier and S. C. Jacobsen, Anal. Chem., 2007, 79, 9471-9477.
38 C.-Y. Chen, A. M. Wo and D.-S. Jong, Lab Chip, 2012, 12, 794-801.
39 K. A. Fosser and R. G. Nuzzo, Anal. Chem., 2003, 75, 5775-5782.
40 A. E. Kamholz and P. Yager, Biophys. J., 2001, 80, 155-160.
41 A. E. Kamholz, E. A. Schilling and P. Yager, Biophys. J., 2001, 80, 1967-1972.
42 J. Comelles, V. Hortiguela, J. Samitier and E. Martinez, Langmuir, 2012, 28, 13688-13697.
43 W. Georgescu, J. Jourquin, L. Estrada, A. R. A. Anderson, V. Quaranta and J. P. Wikswo, Lab Chip, 2007, 8, 238-244.
44 M. D. Estes, J. Yang, B. Duane, S. Smith, C. Brooks, A. Nordquist and F. Zenhausern, Analyst, 2012, 137, 5510-5519.
45 C. Hurth, S. D. Smith, A. R. Nordquist, R. Lenigk, B. Duane, D. Nguyen, A. Surve, M. D. Estes, J. Yang, Z. Cai, X. Chen, F. Zenhausern, A. J. Hopwood, J. G. Lee-Edghill, N. Moran, K. Elliott and G. Tully, Electrophoresis, 2010, 31, 3510-3517.
46 A. J. Hopwood, N. Moran, J. G. Lee-Edghill, J. P. Haley, C. R. McAlister, K. Elliott, P. Koumi, G. Tully, C. Hurth, J. Yang, Z. Cai, A. Nordquist, R. Lenigk, M. D. Estes, X.

Chen, C. Brooks, S. Smith and F. Zenhausern, Anal. Chem., 2010, 82, 6991-6999.
47 A. Lagunas, J. Comelles, E. Martinez and J. Samitier, Langmuir, 2010, 26, 14154-14161.
48 T. H. Steinberg, B. J. Agnew, G. R. Kee, W. Y. Leung, T. Goodman, B. Schulenberg, J. Hendrickson, J. M. Beechem, R. P. HauglandandW. F. Paton, Proteomics, 2003, 3, 1128-1144.
49 M. A. Holden, S. Kumar, E. T. Castellana, A. Beskok and P. S. Cremer, Sens. Actuators, B, 2003, 92, 199-207.
50 M. Srisa-Art, E. C. Dyson, A. J. de Mello and J. B. Edel, Anal. Chem., 2008, 80, 7063-7067.
51 Y.-A. Chen, A. D. King, H.-C. Shih, C.-C. Peng, C.-Y. Wu, W.-H. Liao and Y.-C. Tung, Lab Chip, 2011, 11, 3626-3633.
Estes et al. Phys. Chem. Chem. Phys., 2013, 15, 12805-12814.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure. Specific names of compounds are intended to be exemplary, as it is known that one of ordinary skill in the art can name the same compounds differently.

Every formulation or combination of components described or exemplified herein can be used to practice the invention, unless otherwise stated.

Whenever a range is given in the specification, for example, a physical property range, a size range, a distance range, an area range, a number range, a flow-rate or flow-rate ratio range, dimensionless variable range, temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A microfluidic gradient generator for tuning dynamic components of fluid comprising:
    a first fluid conduit;
    a second fluid conduit,
    an intersection region that fluidically connects the first fluid conduit and the second fluid conduit, the intersection region comprising an intersection opening between the first fluid conduit and the second fluid conduit and a flow-divider that extends in a downstream direction from the intersection opening, wherein the first fluid conduit and the second fluid conduit intersect at an intersection angle relative to each other that is less than 180 degrees;
a source reservoir channel fluidically connected to the intersection region and extending downstream from the intersection opening;
a sink reservoir channel fluidically connected to the intersection region and extending downstream from the intersection opening;
a microchannel array comprising a plurality of microchannels, each microchannel having an inlet end connected to the source reservoir channel and an outlet end connected to the sink reservoir channel, wherein adjacent microchannels are separated from each other by a separation distance, wherein the microchannel array traverses an axial distance along the source reservoir channel;
wherein the first fluid conduit and the second fluid conduit are configured to provide to the intersection region a ratio of a first fluid flow rate to a second fluid flow rate to establish a mixed flow that is substantially laminar, the mixed flow comprising the first fluid and the second fluid in the source reservoir channel; a source reservoir channel gradient; and an array of microfluidic gradients that vary with the ratio of the first fluid flow rate to the second fluid flow rate;
wherein the flow-divider comprises:
an upstream sharp-edged divider that defines the downstream side of the intersection opening;
a downstream reservoir separation section that separates the source and sink reservoir channels;
an expanding central section that connects the upstream sharp-edged divider to the downstream reservoir separation section; and
wherein the microchannel array traverses the downstream reservoir separation section to fluidically connect the source and sink reservoir channels.

2. The microfluidic gradient generator of claim 1, wherein the plurality of microchannels have an axial direction that is substantially perpendicular to an axial direction of the source reservoir channel; and the source reservoir channel and the sink reservoir channel extend along an axial direction, wherein the source reservoir axial direction and the sink reservoir axial direction are substantially parallel to each other and separated by a separation distance through which the array of microchannels traverse.

3. The microfluidic gradient generator of claim 1, wherein:
the microchannels of the microchannel array independently have a cross-sectional area that is less than or equal to 0.1 mm$^2$ and a length that is greater than or equal to 0.1 mm and less than or equal to 1 cm;
the microchannels of the microchannel array independently have a volume that is greater than or equal to 1 nL and less than or equal to 1 mL;
the source and sink reservoir channels each independently have a cross-sectional area that is greater than or equal to 1 mm$^2$ and less than or equal to 1 cm$^2$ and a length that is greater than or equal to 1 mm and less than or equal to 10 cm;
the first and second fluid conduits each independently have a cross-sectional area that is greater than or equal to 1 mm$^2$ and less than or equal to 1 cm$^2$; and
wherein the cross-sectional areas, fluid flow-rates, fluid properties, and microfluidic gradient generator geometry are configured to provide substantially laminar flow at and downstream of the intersection region.

4. A microfluidic gradient generator for tuning dynamic components of fluid comprising:
a first fluid conduit;
a second fluid conduit,
an intersection region that fluidically connects the first fluid conduit and the second fluid conduit, the intersection region comprising an intersection opening between the first fluid conduit and the second fluid conduit and a flow-divider that extends in a downstream direction from the intersection opening, wherein the first fluid conduit and the second fluid conduit intersect at an intersection angle relative to each other that is less than 180 degrees;
a source reservoir channel fluidically connected to the intersection region and extending downstream from the intersection opening;
a sink reservoir channel fluidically connected to the intersection region and extending downstream from the intersection opening;
a microchannel array comprising a plurality of microchannels, each microchannel having an inlet end connected to the source reservoir channel and an outlet end connected to the sink reservoir channel, wherein adjacent microchannels are separated from each other by a separation distance, wherein the microchannel array traverses an axial distance along the source reservoir channel;
wherein the first fluid conduit and the second fluid conduit are configured to provide to the intersection region a ratio of a first fluid flow rate to a second fluid flow rate to establish a mixed flow that is substantially laminar, the mixed flow comprising the first fluid and the second fluid in the source reservoir channel; a source reservoir channel gradient; and an array of microfluidic gradients that vary with the ratio of the first fluid flow rate to the second fluid flow rate; and
wherein the microarray of channels are formed in a base plate and the source and sink reservoir in a top plate, and the plate and top plate are connected to form the microarray of channels positioned in a different plane from the source and the sink reservoir channels; and the base plate and the top plate are connected with an adhesive.

5. The microfluidic gradient generator of claim 1, wherein each microchannel inlet end is positioned on a bottom surface of the source reservoir channel and each microchannel outlet end is positioned on a bottom surface of the sink reservoir channel.

6. The microfluidic gradient generator of claim 1, wherein the first fluid conduit and sink reservoir channel form a mirror image of the second fluid conduit and source reservoir channel and the sink and source reservoir channels are interchangeable for an inverse of the ratio of the first fluid flow rate to the second fluid flow rate.

7. The microfluidic gradient generator of claim 1, wherein the array of microfluidic gradients or a microfluidic gradient of the array has a shape that is not-linear.

8. The microfluidic gradient generator of claim 1, wherein the array of microfluidic gradients is selected from the group consisting of:
concentration of a material suspended in the first fluid;
concentration of a material suspended in the second fluid;
ratio of the first fluid amount to the second fluid amount;
temperature;
electrical conductivity;
binding event;
amplification of template biomolecules;

concentration of a product produced by a substrate-enzyme reaction in the mixed fluid of the source reservoir channel;

concentration of a bioproduct produced from combination of a first biomolecule in the source reservoir channel and a second biomolecule in the microchannels; and a biological event characterized by an interaction between a material suspended or formed in the mixed fluid flow and a biological cell in the microarray.

9. The microfluidic gradient generator of claim 1, further comprising a flow-rate controller to vary the ratio of the first fluid flow rate to the second fluid flow rate, wherein the flow-rate controller provides a microfluidic gradient in a microchannel having a shape and a magnitude that is temporally adjustable.

10. The microfluidic gradient generator of claim 1, further comprising a first fluid in the first fluid conduit and a second fluid in the second fluid conduit, wherein a chemical or a biochemical is transported in the first fluid, the second fluid, or both, and the array of microfluidic gradients is concentration of the chemical or biochemical in each of the microchannels.

11. The microfluidic gradient generator of claim 10, further comprising biological cells supported by a surface of the microchannel array for testing the effect of different concentrations of the chemical or biochemical on the biological cells.

12. The microfluidic gradient generator of claim 10 wherein the chemical or biochemical is selected from the group consisting of:
- a cancer treatment candidate;
- a reagent compound for performing a biological assay reaction;
- a drug for toxicity screening;
- a growth factor for cellular differentiation;
- a ligand that specifically binds a surface receptor;
- an immunoactive agent for chemotaxis or immunological study;
- a chemical for a polymerization reaction;
- a chemical for a catalytic reaction; and
- a reagent for amplification of polynucleotides by polymerase chain reaction.

13. The microfluidic gradient generator of claim 1, wherein the array of microfluidic gradients corresponds to a physical parameter selected from the group consisting of temperature, pH, oxygen level, electrical conductivity, a rheological property, electromagnetic property, light emission, light absorption, and adsorption.

14. A method of generating an array of microfluidic gradients, the method comprising the steps of:
providing the microfluidic generator of claim 1;
flowing a first fluid in the first fluid conduit at a first fluid flow rate ($Q_1$);
flowing a second fluid in the second fluid conduit at a second fluid flow rate ($Q_2$);
introducing the first fluid and the second fluid to the intersection region, having an inlet fluid flow ratio, $Q_i$, calculated as: $Q_i=Q_1/Q_2$, wherein the first fluid conduit and the second fluid conduit intersect at the intersection angle relative to each other that is less than 180 degrees;
selecting the inlet fluid flow ratio to generate a mixed flow comprising the first fluid and the second fluid, wherein the mixed flow is substantially laminar in the source reservoir channel fluidically connected to the intersection region to provide the source reservoir channel gradient, wherein the source reservoir channel gradient varies with a longitudinal distance from the intersection region by diffusion between the first fluid and the second fluid in the source reservoir channel;
introducing the mixed flow from the source reservoir channel to the array of microchannels;
wherein the sink reservoir channel is fluidically connected to the intersection region, and the sink reservoir channel and source reservoir channel are separated from each other by the microchannel array; and
wherein the source reservoir channel gradient provides the array of microfluidic gradients in the array of microchannels that is tunable by varying the inlet fluid flow ratio, thereby generating a tunable array of microfluidic gradients.

15. The method of claim 14, wherein the inlet fluid flow ratio is greater than or equal to 2 and less than or equal to 1000, and fluid flow in each of the intersection region, source reservoir channel and sink reservoir channel is substantially laminar, and each microfluidic gradient in a microchannel is different from another microfluidic gradient in another microchannel.

16. The method of claim 14, further comprising the step of filling the sink reservoir channel with the first fluid and providing an excess of the first fluid to the source reservoir channel to provide the mixed stream flow in the source reservoir channel with the first fluid providing a diffusive barrier between the second fluid and the microchannel inlet ends.

17. The method of claim 14, further comprising the step of adjusting the inlet fluid flow ratio to tune the array of microfluidic gradients.

18. The method of claim 14, further comprising:
providing biological cells to the array of microchannels;
supplying a chemical or biochemical to the second fluid;
selecting the inlet fluid flow ratio to provide the source reservoir channel gradient that corresponds to concentration of the bioactive agent at the microfluidic array inlet ends; and
examining an effect on the biological cells at different concentrations of the chemical or biochemical.

* * * * *